United States Patent
Tang

(10) Patent No.: US 10,702,235 B2
(45) Date of Patent: Jul. 7, 2020

(54) SYSTEMS AND METHODS FOR MEDICAL IMAGING

(71) Applicant: SHENZHEN UNITED IMAGING HEALTHCARE CO., LTD., Shenzhen, Guangdong (CN)

(72) Inventor: Bing Tang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 170 days.

(21) Appl. No.: 16/024,111

(22) Filed: Jun. 29, 2018

(65) Prior Publication Data

US 2018/0353151 A1  Dec. 13, 2018

Related U.S. Application Data

(63) Continuation of application No. PCT/CN2018/090452, filed on Jun. 8, 2018.

(30) Foreign Application Priority Data

Jun. 8, 2017 (CN) .......................... 2017 1 0426662
Nov. 28, 2017 (CN) .......................... 2017 1 1218942

(51) Int. Cl.
*A61B 6/00* (2006.01)
*G01N 23/046* (2018.01)
*G06T 11/00* (2006.01)

(52) U.S. Cl.
CPC ............ *A61B 6/545* (2013.01); *A61B 6/4411* (2013.01); *A61B 6/469* (2013.01); *A61B 6/542* (2013.01);

(Continued)

(58) Field of Classification Search
CPC ........... A61B 6/00; A61B 6/545; A61B 6/469; A61B 6/542; A61B 6/547; A61B 6/4411;

(Continued)

(56) References Cited

U.S. PATENT DOCUMENTS 10,004,564 B1 * 6/2018 Beck ...................... A61B 6/547
2003/0179851 A1   9/2003 Ishikawa (Continued)

FOREIGN PATENT DOCUMENTS

| CN | 101123911 A | 2/2008 |
| CN | 104173066 A | 12/2014 |

(Continued)

OTHER PUBLICATIONS

The Second Office Action in Chinese Application No. 201710426662.9 dated Feb. 3, 2020, 13 pages.

(Continued)

*Primary Examiner* — Jurie Yun
(74) *Attorney, Agent, or Firm* — Metis IP LLC

(57) ABSTRACT

A method may include obtaining an initial image that is captured by scanning a scan object using the imaging device. The method may also include performing an iteration process including one or more iterations. Each of the one or more iterations may include determining, according to a thickness model, an equivalent thickness associated with the scan object based on a brightness of a first image and the target brightness, determining one or more second exposure parameters corresponding to the equivalent thickness and the target brightness based on the thickness model, and generating a second image by directing the imaging device to scan the scan object based on the one or more second exposure parameters using the imaging device. The first (Continued)

image may be the initial image in a first iteration of the one or more iterations or an image generated in a previous iteration.

20 Claims, 10 Drawing Sheets

(52) U.S. Cl.
CPC .......... *G01N 23/046* (2013.01); *G06T 11/005* (2013.01); *A61B 6/4441* (2013.01); *A61B 6/4452* (2013.01); *A61B 6/547* (2013.01); *A61B 6/563* (2013.01); *G01N 2223/419* (2013.01); *G06T 2211/40* (2013.01)

(58) Field of Classification Search
CPC ........ A61B 6/54; G01N 23/046; G01N 23/04; G06T 11/00; G06T 11/005; G06T 2211/40
USPC .................................. 378/4, 8, 62, 98.7, 210
See application file for complete search history.

(56) References Cited

U.S. PATENT DOCUMENTS

| | | |
|---|---|---|
| 2007/0238963 A1 | 10/2007 | Kaminaga et al. |
| 2012/0027169 A1 | 2/2012 | Nakayama |
| 2013/0228694 A1 | 9/2013 | Nakatsugawa et al. |
| 2016/0100816 A1 | 4/2016 | Jung et al. |
| 2017/0086777 A1 | 3/2017 | Kawamura |
| 2017/0150938 A1 | 6/2017 | Wang |
| 2018/0199907 A1 | 7/2018 | Hatakeyama |

FOREIGN PATENT DOCUMENTS

| | | |
|---|---|---|
| CN | 104238905 A | 12/2014 |
| CN | 105451655 A | 3/2016 |
| CN | 105528764 A | 4/2016 |
| CN | 106214171 A | 12/2016 |
| CN | 106413236 A | 2/2017 |
| CN | 107049346 A | 8/2017 |
| CN | 107811646 A | 3/2018 |
| CN | 110101399 A | 8/2019 |
| EP | 2813182 A1 | 12/2014 |
| JP | 2014057664 A | 4/2014 |
| JP | 2015103991 A | 6/2015 |
| JP | 2017060544 A | 3/2017 |

OTHER PUBLICATIONS

International Search Report in PCT/CN2018/090452 dated Sep. 4, 2018, 6 pages.
Written Opinion in PCT/CN2018/090452 dated Sep. 4, 2018, 7 pages.
The Extended European Search Report in European Application No. 18814186.5 dated Apr. 30, 2020, 7 pages.

* cited by examiner

SYSTEMS AND METHODS FOR MEDICAL IMAGING

CROSS-REFERENCE TO RELATED APPLICATIONS

This application is a continuation of International Application No. PCT/CN2018/090452 filed on Jun. 8, 2018, which claims priority to Chinese Patent Application No. 201710426662.9 filed on Jun. 8, 2017, and Chinese Patent Application No. 201711218942.7 filed on Nov. 28, 2017, the contents of each of which are hereby incorporated by reference.

TECHNICAL FIELD

The present disclosure generally relates to medical imaging, and more particularly, systems and methods for adjusting one or more imaging parameters of an X-ray radiography device.

BACKGROUND

X-ray radiography is widely used in medical imaging and diagnosis. Typical X-ray radiography devices may include a computed tomography (CT) device, a digital radiography (DR) device, a C-arm X-ray device, and so on. To perform a scan using the existing technology, an imaging technician need manually adjust one or more imaging parameters associated with an X-ray generator and/or a detector of an X-ray radiography device for multiple times in order to obtain a desired image. Manual adjustment may be time-consuming and inaccurate. Therefore, it is desired to provide X-ray radiography systems and methods for medical imaging in which the one or more imaging parameters may be adjusted automatically.

SUMMARY

According to a first aspect of the present disclosure, a method for imaging using an imaging device may include one or more of the following operations. One or more processors may obtain location information associated with an X-ray generator of the imaging device, a detector of the imaging device, and a region of interest (ROI) of a scan object. The one or more processors may determine image magnification based on the location information. According to image quality conditions, the one or more processors may determine one or more first parameters of the detector and one or more second parameters of the X-ray generator based on the image magnification. The one or more first parameters of the detector may be different from one or more first preset parameters of the detector. The one or more second parameters of the X-ray generator may be different from one or more second preset parameters of the X-ray generator. The one or more processors may generate an image of the image magnification by directing the imaging device to scan the ROI based on the one or more first parameters of the detector and the one or more second parameters of the X-ray generator.

According to another aspect of the present disclosure, a system for medical imaging may include an imaging device including an X-ray generator and a detector, one or more storage media, and one or more processors configured to communicate with the one or more storage media. The one or more storage media may include a set of instructions. When the one or more processors executing the set of instructions, the one or more processors may be directed to perform one or more of the following operations. The one or more processors may obtain location information associated with the X-ray generator of the imaging device, the detector of the imaging device, and a region of interest (ROI) of a scan object. The one or more processors may determine image magnification based on the location information. According to image quality conditions, the one or more processors may determine one or more first parameters of the detector and one or more second parameters of the X-ray generator based on the image magnification. The one or more first parameters of the detector may be different from one or more first preset parameters of the detector. The one or more second parameters of the X-ray generator may be different from one or more second preset parameters of the X-ray generator. The one or more processors may generate an image of the image magnification by directing the imaging device to scan the ROI based on the one or more first parameters of the detector and the one or more second parameters of the X-ray generator.

According to yet another aspect of the present disclosure, a system for imaging using an imaging device may include an information acquisition block configured to obtain location information associated with an X-ray generator of the imaging device, a detector of the imaging device, and a region of interest (ROI) of a scan object. The system may also include a first magnification determination block configured to determine image magnification based on the location information. The system may also include a parameter determination block configured to determine, according to image quality conditions, one or more first parameters of the detector and one or more second parameters of the X-ray generator based on the image magnification, and generate an image of the image magnification by directing the imaging device to scan the ROI based on the one or more first parameters of the detector and the one or more second parameters of the X-ray generator. The one or more first parameters of the detector may be different from one or more first preset parameters of the detector. The one or more second parameters of the X-ray generator may be different from one or more second preset parameters of the X-ray generator.

According to yet another aspect of the present disclosure, a non-transitory computer readable medium may comprise at least one set of instructions for imaging using an imaging device. The at least one set of instructions may be executed by one or more processors of a computer server. The one or more processors may obtain location information associated with an X-ray generator of the imaging device, a detector of the imaging device, and a region of interest (ROI) of a scan object. The one or more processors may determine image magnification based on the location information. According to image quality conditions, the one or more processors may determine one or more first parameters of the detector and one or more second parameters of the X-ray generator based on the image magnification. The one or more first parameters of the detector may be different from one or more first preset parameters of the detector. The one or more second parameters of the X-ray generator may be different from one or more second preset parameters of the X-ray generator. The one or more processors may generate an image of the image magnification by directing the imaging device to scan the ROI based on the one or more first parameters of the detector and the one or more second parameters of the X-ray generator.

According to yet another aspect of the present disclosure, a method for imaging using an imaging device may include one or more of the following operations. One or more processors may obtain one or more image quality parameters. The one or more processors may determine one or more first parameters of a detector of the imaging device and one or more second parameters of an X-ray generator of the imaging device based on the one or more image quality parameters. The one or more first parameters of the detector may be different from one or more first preset parameters of the detector. The one or more second parameters of the X-ray generator may be different from one or more second preset parameters of the X-ray generator. The one or more processors may determine image magnification based on the one or more first parameters of the detector and the one or more second parameters of the X-ray generator. The one or more processors may determine location information associated with the X-ray generator, the detector, and a region of interest (ROI) of a scan object. The one or more processors may adjust, based on the location information, at least one of the X-ray generator, the detector, or the ROI.

According to yet another aspect of the present disclosure, a system for medical imaging may include an imaging device including an X-ray generator and a detector, one or more storage media, and one or more processors configured to communicate with the one or more storage media. The one or more storage media may include a set of instructions. When the one or more processors executing the set of instructions, the one or more processors may be directed to perform one or more of the following operations. The one or more processors may obtain one or more image quality parameters. The one or more processors may determine one or more first parameters of the detector of the imaging device and one or more second parameters of the X-ray generator of the imaging device based on the one or more image quality parameters. The one or more first parameters of the detector may be different from one or more first preset parameters of the detector. The one or more second parameters of the X-ray generator may be different from one or more second preset parameters of the X-ray generator. The one or more processors may determine image magnification based on the one or more first parameters of the detector and the one or more second parameters of the X-ray generator. The one or more processors may determine location information associated with the X-ray generator, the detector, and a region of interest (ROI) of a scan object. The one or more processors may adjust, based on the location information, at least one of the X-ray generator, the detector, or the ROI.

According to yet another aspect of the present disclosure, a system for imaging using an imaging device may include an imaging parameter obtaining block configured to obtain one or more image quality parameters and determine one or more first parameters of a detector of the imaging device and one or more second parameters of an X-ray generator of the imaging device based on the one or more image quality parameters. The one or more first parameters of the detector may be different from one or more first preset parameters of the detector. The one or more second parameters of the X-ray generator may be different from one or more second preset parameters of the X-ray generator. The system may also include a second magnification determination block configured to determine image magnification based on the one or more first parameters of the detector and the one or more second parameters of the X-ray generator. The system may also include a location determination block configured to determine location information associated with the X-ray generator, the detector, and a region of interest (ROI) of a scan object and adjust, based on the location information, at least one of the X-ray generator, the detector, or the ROI.

According to yet another aspect of the present disclosure, a non-transitory computer readable medium may comprise at least one set of instructions for imaging using an imaging device. The at least one set of instructions may be executed by one or more processors of a computer server. The one or more processors may obtain one or more image quality parameters. The one or more processors may determine one or more first parameters of a detector of the imaging device and one or more second parameters of an X-ray generator of the imaging device based on the one or more image quality parameters. The one or more first parameters of the detector may be different from one or more first preset parameters of the detector. The one or more second parameters of the X-ray generator may be different from one or more second preset parameters of the X-ray generator. The one or more processors may determine image magnification based on the one or more first parameters of the detector and the one or more second parameters of the X-ray generator. The one or more processors may determine location information associated with the X-ray generator, the detector, and a region of interest (ROI) of a scan object. The one or more processors may adjust, based on the location information, at least one of the X-ray generator, the detector, or the ROI.

According to yet another aspect of the present disclosure, a method for imaging using an imaging device may include one or more of the following operations. One or more processors may obtain an initial image that is captured by scanning a scan object based on one or more initial exposure parameters using the imaging device. The one or more processors may perform an iteration process including one or more iterations until an image whose brightness satisfies a target brightness is generated. Each of the one or more iterations may include determining, according to a thickness model, an equivalent thickness associated with the scan object based on a brightness of a first image and the target brightness. The first image may be the initial image in a first iteration of the one or more iterations or an image generated in a previous iteration. The first image may be associated with one or more first exposure parameters. Each of the one or more iterations may also include determining one or more second exposure parameters corresponding to the equivalent thickness and the target brightness based on the thickness model. Each of the one or more iterations may also include generating a second image by directing the imaging device to scan the scan object based on the one or more second exposure parameters using the imaging device.

According to yet another aspect of the present disclosure, a system for medical imaging may include an imaging device including an X-ray generator and a detector, one or more storage media, and one or more processors configured to communicate with the one or more storage media. The one or more storage media may include a set of instructions. When the one or more processors executing the set of instructions, the one or more processors may be directed to perform one or more of the following operations. The one or more processors may obtain an initial image that is captured by scanning a scan object based on one or more initial exposure parameters using the imaging device. The one or more processors may perform an iteration process including one or more iterations until an image whose brightness satisfies a target brightness is generated. Each of the one or more iterations may include determining, according to a thickness model, an equivalent thickness associated with the scan object based on a brightness of a first image and the target brightness. The first image may be the initial image in a first iteration of the one or more iterations or an image generated in a previous iteration. The first image may be associated with one or more first exposure parameters. Each of the one or more iterations may also include determining one or more second exposure parameters corresponding to the equivalent thickness and the target brightness based on the thickness model. Each of the one or more iterations may also include generating a second image by directing the imaging device to scan the scan object based on the one or more second exposure parameters using the imaging device.

According to yet another aspect of the present disclosure, a system for imaging using an imaging device may include an acquisition unit configured to obtain an initial image that is captured by scanning a scan object based on one or more initial exposure parameters using the imaging device. The system may also include an equivalent thickness determination unit configured to determine, according to a thickness model, an equivalent thickness associated with the scan object based on a brightness of a first image and the target brightness. The first image may be the initial image in a first iteration of one or more iterations of an iteration process or an image generated in a previous iteration. The first image may be associated with one or more first exposure parameters. The system may also include an exposure parameter determination unit configured to determine one or more second exposure parameters corresponding to the equivalent thickness and the target brightness based on the thickness model. The system may also include a scanning unit configured to generate a second image by directing the imaging device to scan the scan object based on the one or more second exposure parameters using the imaging device.

According to yet another aspect of the present disclosure, a non-transitory computer readable medium may comprise at least one set of instructions for imaging using an imaging device. The at least one set of instructions may be executed by one or more processors of a computer server. The one or more processors may obtain an initial image that is captured by scanning a scan object based on one or more initial exposure parameters using the imaging device. The one or more processors may perform an iteration process including one or more iterations until an image whose brightness satisfies a target brightness is generated. Each of the one or more iterations may include determining, according to a thickness model, an equivalent thickness associated with the scan object based on a brightness of a first image and the target brightness. The first image may be the initial image in a first iteration of the one or more iterations or an image generated in a previous iteration. The first image may be associated with one or more first exposure parameters. Each of the one or more iterations may also include determining one or more second exposure parameters corresponding to the equivalent thickness and the target brightness based on the thickness model. Each of the one or more iterations may also include generating a second image by directing the imaging device to scan the scan object based on the one or more second exposure parameters using the imaging device.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
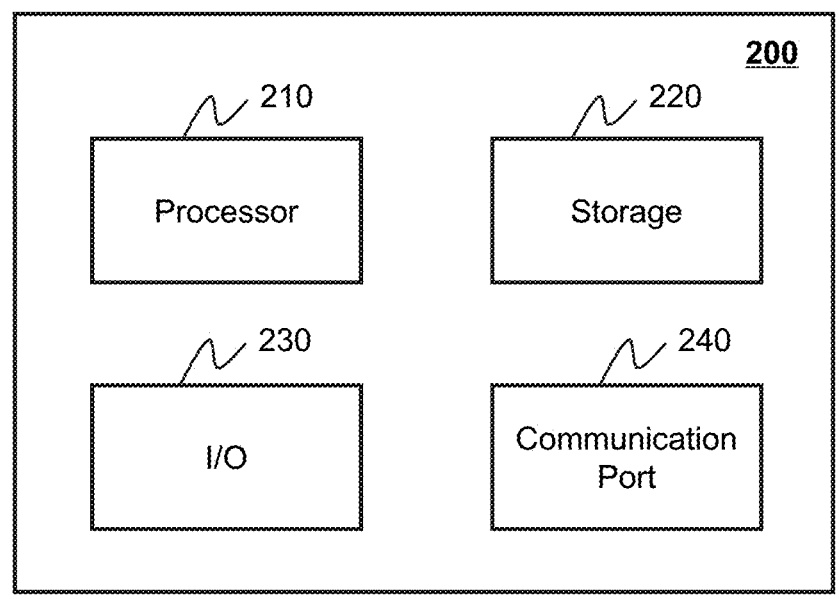
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding an imaging process. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

Figure 1:
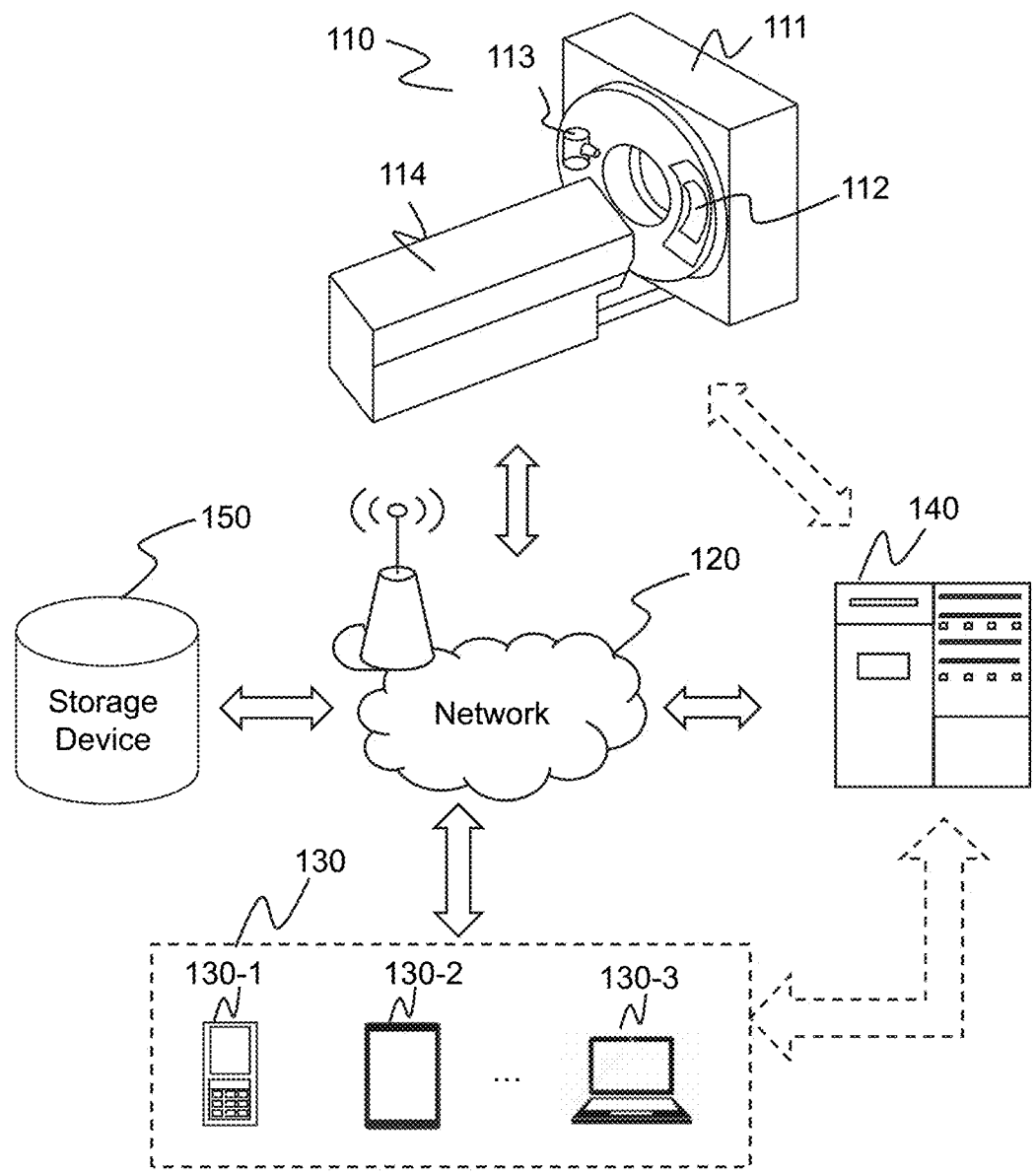
FIG. 1 is a schematic diagram illustrating an exemplary imaging system according to some embodiments of the present disclosure.

FIG. 1 is a schematic diagram illustrating an exemplary imaging system according to some embodiments of the present disclosure. In some embodiments, the imaging system 100 may be applied to any application scenario in which X-rays are used for generating images and/or providing treatment, such as a computed tomography (CT) system, a digital radiography (DR) system, a C-arm X-ray system, a computed tomography-positron emission tomography (CT-PET) system, or the like, or a combination thereof.

As illustrated in FIG. 1, the imaging system 100 may include an imaging device 110, a network 120, one or more terminals 130, a processing device 140, and a storage device 150. The components in the imaging system 100 may be connected in one or more of various ways. Merely by way of example, the imaging device 110 may be connected to the processing device 140 through the network 120. As another example, the imaging device 110 may be connected to the processing device 140 directly as indicated by the bi-directional arrow in dotted lines linking the imaging device 110 and the processing device 140. As a further example, the storage device 150 may be connected to the processing device 140 directly or through the network 120. As still a further example, the terminal 130 may be connected to the processing device 140 directly (as indicated by the bi-directional arrow in dotted lines linking the terminal 130 and the processing device 140) or through the network 120.

In some embodiments, the imaging device 110 may include a computed tomography (CT) scanner, a digital radiography (DR) scanner, a C-arm X-ray scanner, a digital substraction angiography (DSA) scanner, a dynamic spatial reconstructor (DSR) scanner, an X-ray microscopy scanner, a multi-modality scanner, or the like, or a combination thereof. Exemplary multi-modality scanners may include a computed tomography-positron emission tomography (CT-PET) scanner, a computed tomography-magnetic resonance imaging (CT-MRI) scanner, etc.

The imaging device 110 may include a gantry 111, a detector 112, an X-ray generator 113, and a scanning table 114. The detector 112 and the X-ray generator 113 may be oppositely mounted on the gantry 111. A scan object may be placed on the scanning table 114 and moved into a detection tunnel (e.g., a space between the detector 112 and the X-ray generator 113) of the imaging device 110. The scan object may be biological or non-biological. Merely by way of example, the scan object may include a patient, a man-made object, etc. As another example, the scan object may include a specific portion, organ, and/or tissue of the patient. For example, the scan object may include head, brain, neck, body, shoulder, arm, thorax, cardiac, stomach, blood vessel, soft tissue, knee, feet, or the like, or any combination thereof. In the present disclosure, "subject", "object" or "scan object" are used interchangeably.

The X-ray generator 113 may emit radiation rays to scan the scan object that is placed on the scanning table 114. The radiation rays may include X-rays, γ-rays, α-rays, ultraviolet, laser, neutron, proton, or the like, or a combination thereof. The detector 112 may receive the radiation rays passed through the scan object. In some embodiments, the detector 112 may include a plurality of detector units, which may be arranged in a channel direction and a row direction.

The detector 112 may include a scintillation detector (e.g., a cesium iodide detector) or a gas detector.

The network 120 may facilitate exchange of information and/or data. In some embodiments, one or more components of the imaging system 100 (e.g., the imaging device 110, the terminal 130, the processing device 140, or the storage device 150) may send information and/or data to another component(s) in the imaging system 100 via the network 120. For example, the processing device 140 may obtain, via the network 120, an image from the storage device 150. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the imaging system 100 may be connected to the network 120 to exchange data and/or information.

The terminal 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 130 may remotely operate the imaging device 110. In some embodiments, the terminal 130 may operate the imaging device 110 via a wireless connection. In some embodiments, the terminal 130 may receive information and/or instructions inputted by a user, and send the received information and/or instructions to the imaging device 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

In some embodiments, the processing device 140 may process data obtained from the imaging device 110, the terminal 130, or the storage device 150. For example, the processing device 140 may determine image magnification based on location information associated with the X-ray generator 113 of the imaging device 110, the detector 112 of the imaging device 110, and the ROI of the scan object, and determine one or more first parameters of the detector 112 and one or more second parameters of the X-ray generator 113 based on the image magnification. The processing device 140 may further generate an image of the image magnification by directing the imaging device 110 to scan the ROI according to the one or more first parameters and the one or more second parameters. As another example, the processing device 140 may determine one or more first parameters of the detector 112 and one or more second parameters of the X-ray generator 113 based on one or more image quality parameters (e.g., target brightness, an image contrast, or an image resolution), and determine image magnification based on the one or more first parameters and the one or more second parameters. The processing device 140 may determine location information associated with the X-ray generator 113, the detector 112, and the ROI of the scan object, and adjust the X-ray generator 113, the detector 112, or the ROI based on the location information to generate an image of the image magnification. As a further example, the processing device 140 may generate an image that satisfies target brightness according to one or more exposure parameters (e.g., a tube voltage and/or a tube current). The processing device 140 may be a central processing unit (CPU), a digital signal processor (DSP), a system on a chip (SoC), a microcontroller unit (MCU), or the like, or any combination thereof.

In some embodiments, the processing device 140 may be a single server or a server group. The server group may be centralized or distributed. In some embodiments, the processing device 140 may be local or remote. For example, the processing device 140 may access information and/or data stored in the imaging device 110, the terminal 130, and/or the storage device 150 via the network 120. As another example, the processing device 140 may be directly connected to the imaging device 110, the terminal 130, and/or the storage device 150, to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal 130 and/or the processing device 140. For example, the storage device 150 may store one or more images obtained from the processing device 140. In some embodiments, the storage device 150 may store data and/or instructions that the processing device 140 may execute or use to perform exemplary methods described in the present disclosure. For example, the storage device 150 may store data and/or instructions that the processing device 140 may execute or use to generate an image that satisfies target brightness. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the imaging system 100 (e.g., the terminal 130, the processing device 140). One or more components of the imaging system 100 may access the data or instructions stored in the storage device 150 via the network 120. In some embodiments, the storage device 150 may be directly connected to or communicate with one or more components of the imaging system 100 (e.g., the terminal 130, the processing device 140). In some embodiments, the storage device 150 may be part of the processing device 140.

FIG. 2 is a schematic diagram illustrating hardware and/or software components of an exemplary computing device according to some embodiments of the present disclosure. As illustrated in FIG. 2, the computing device 200 may include a processor 210, a storage 220, an input/output (I/O) 230, and a communication port 240. In some embodiments, the processing device 140 and/or the terminal 130 may be implemented on the computing device 200.

The processor 210 may execute computer instructions (program code) and, when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the imaging device 110, the terminal 130, the storage device 150, and/or any other component of the imaging system 100. For example, the processor 210 may obtain an image from the storage device 150, determine one or more exposure parameters based on the image, and generate another image that satisfies target brightness under the one or more exposure parameters. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the imaging device 110, the terminal 130, the storage device 150, or any other component of the imaging system 100. In some embodiments, the storage 220 may include a mass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program (e.g., in the form of computer-executable instructions) for the processing device 140 for determining one or more first parameters of the X-ray generator 113 and/or one or more second parameters of the detector 112. As another example, the storage 220 may store a program (e.g., in the form of computer-executable instructions) for the processing device 140 for generating an image that satisfies target brightness.

The I/O 230 may input or output signals, data, and/or information. In some embodiments, the I/O 230 may enable user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the imaging device 110, the terminal 130, or the storage device 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
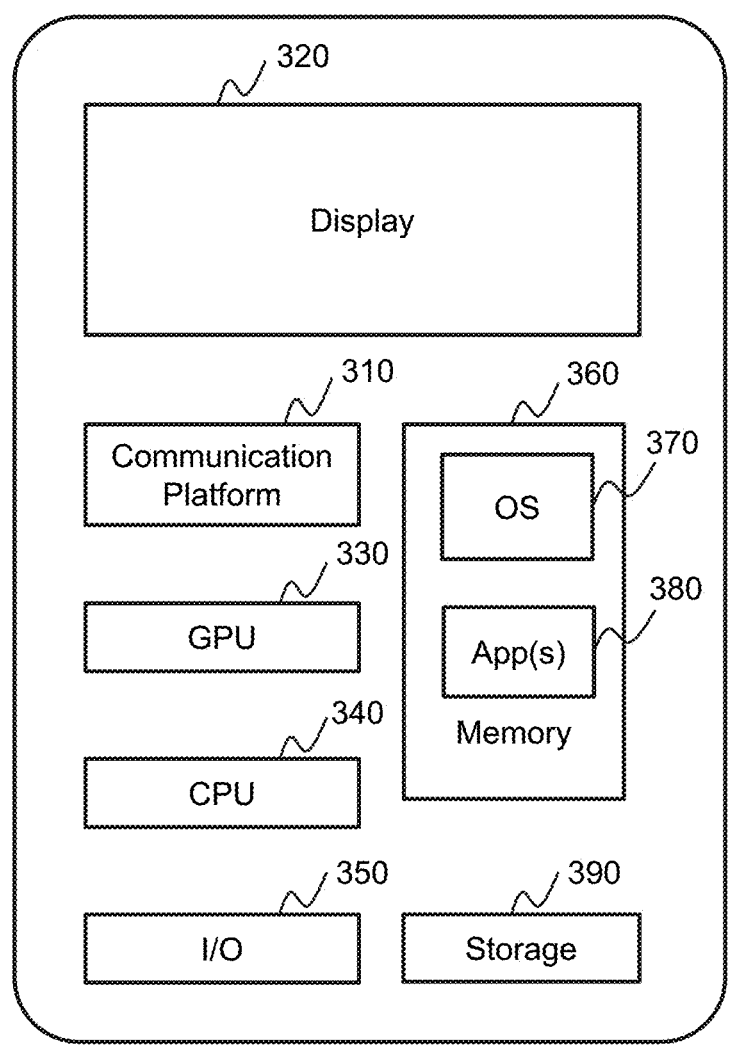
FIG. 3 is a schematic diagram illustrating hardware and/or software components of an exemplary mobile device according to some embodiments of the present disclosure.

FIG. 3 is a schematic diagram illustrating hardware and/or software components of a mobile device according to some embodiments of the present disclosure. In some embodiments, the processing device 140 and/or the terminal 130 may be implemented on the computing device 200. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate high-quality image of a scan object as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
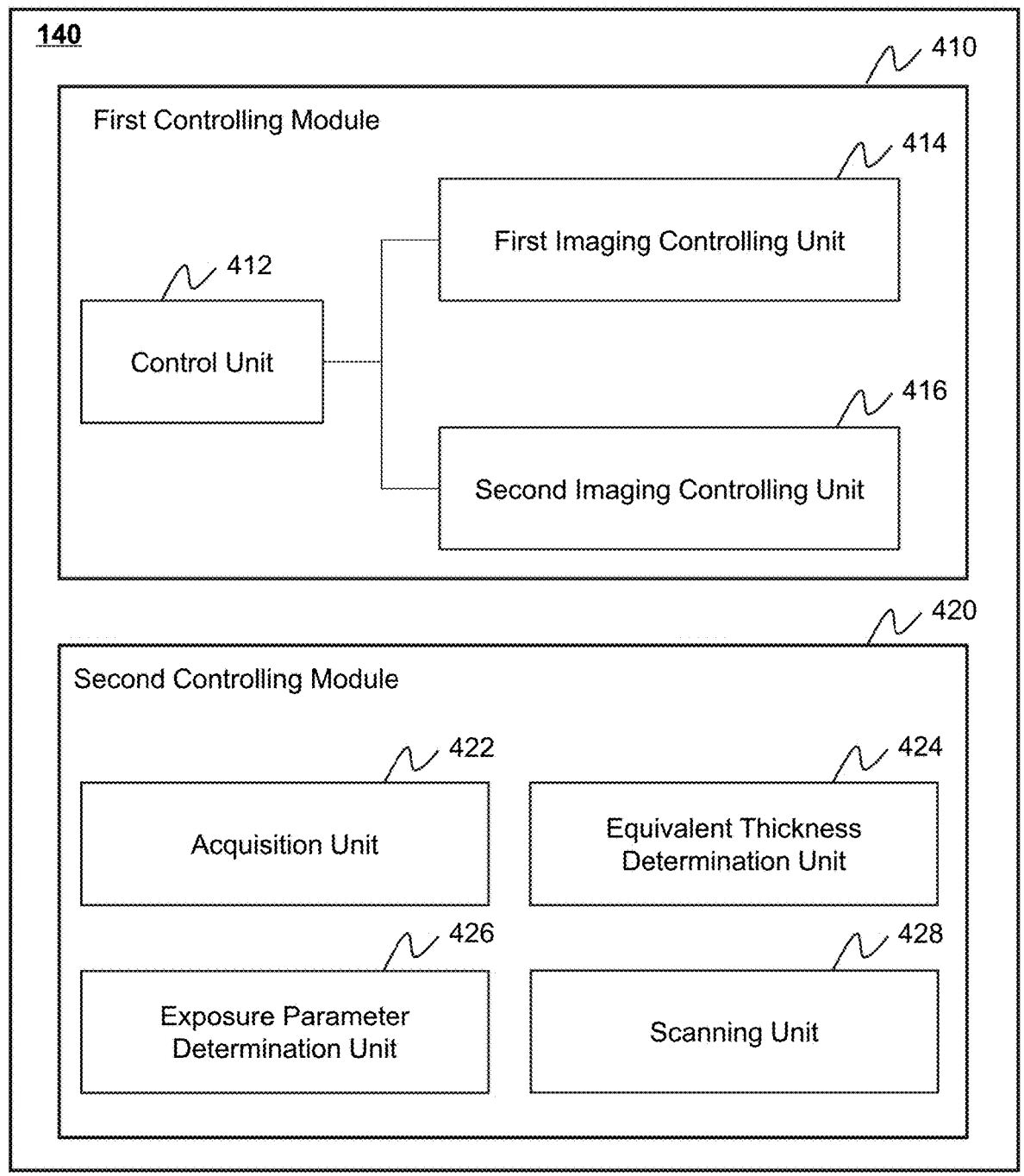
FIG. 4 is a block diagram illustrating an exemplary processing device according to some embodiments of the present disclosure.

FIG. 4 is a schematic diagram illustrating an exemplary processing device 140 according to some embodiments of the present disclosure. The processing device 140 may include a first controlling module 410 and a second controlling module 420. At least a portion of the processing device 140 may be implemented on the computing device 200 as illustrated in FIG. 2 or the mobile device 300 as illustrated in FIG. 3.

The first controlling module 410 may be configured to adjust one or more imaging parameters (e.g., a location of the X-ray generator 113 of the imaging device 110, a location of the detector 112 of the imaging device 110, a location of an ROI of the scan object, one or more parameters of the X-ray generator 113, or one or more parameters of the detector 112) associated with the imaging device 110 to generate an image satisfying image magnification. The first controlling module 410 may include a control unit 412, a first imaging controlling unit 414, and a second imaging controlling unit 416.

The control unit 412 may be configured to determine which of the first imaging controlling unit 414 and the second imaging controlling unit 416 to adjust the one or more imaging parameters associated with the imaging device 110 to generate an image satisfying desired image magnification. In some embodiments, the control unit 412 may determine which of the first imaging controlling unit 414 and the second imaging controlling unit 416 needs to act in the adjustment of the one or more imaging parameters associated with the imaging device 110 in order to generate an image satisfying the desired image magnification based on a user instruction. For example, a user (e.g., a doctor, an imaging technician, or an operator) of the imaging system 100 may input, for example, through the I/O 230 in FIG. 2 or the I/O 350 in FIG. 3, an instruction to let the first imaging controlling unit 414 adjust the one or more imaging parameters associated with the imaging device 110 to generate an image satisfying the desired image magnification, the control unit 412 may select the first imaging controlling unit 414 to adjust the one or more imaging parameters associated with the imaging device 110 to generate an image satisfying the desired image magnification based on the user instruction. In some embodiments, the control unit 412 may determine which of the first imaging controlling unit 414 and the second imaging controlling unit 416 needs to act in the adjustment of the one or more imaging parameters associated with the imaging device 110 to generate an image satisfying the desired image magnification automatically. For example, when the user of the imaging system 100 inputs preset location information associated with the X-ray generator 113, the detector 112, and the ROI of the scan object, the control unit 412 may determine the first imaging controlling unit 414 to adjust the one or more imaging parameters associated with the imaging device 110 to generate an image satisfying the desired image magnification automatically.

Figure 7:
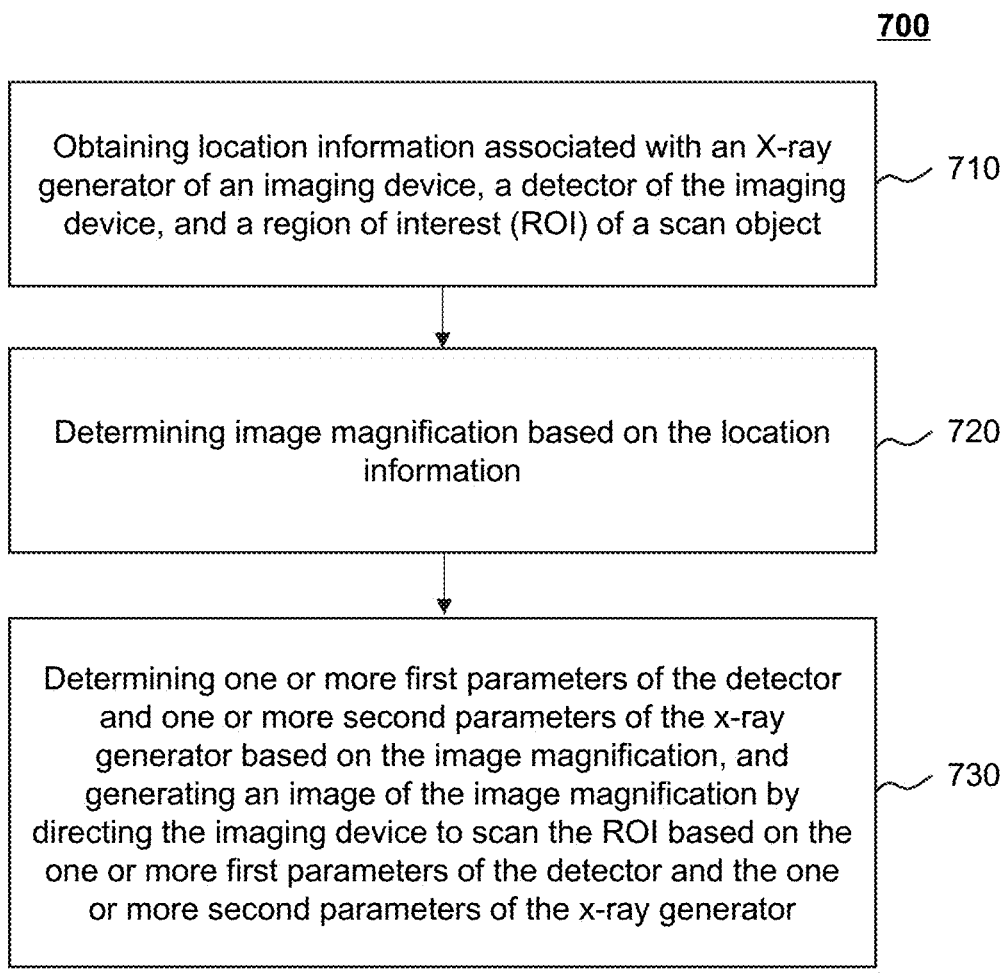
FIG. 7 is a flowchart illustrating an exemplary process for medical imaging according to some embodiments of the present disclosure.

The first imaging controlling unit 414 may be configured to perform process 700 in FIG. 7 to determine, based on location information associated with the X-ray generator 113, the detector 112, and the ROI of the scan object, image magnification, and one or more image quality parameters, one or more first parameters of the detector 112 and one or more second parameters of the X-ray generator 113. More descriptions regarding the first imaging controlling unit 414 may be found elsewhere in the present disclosure (e.g., the description in connection with FIG. 5 and/or the process 700 in FIG. 7).

Figure 8:
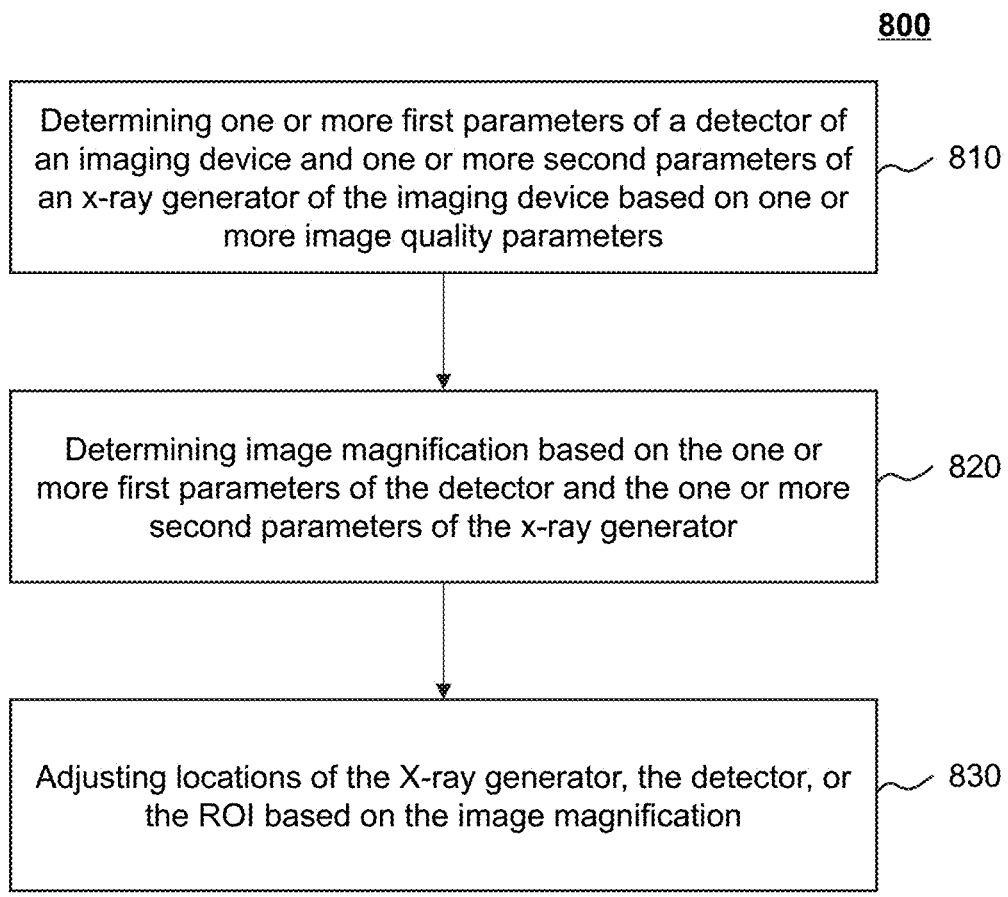
FIG. 8 is a flowchart illustrating an exemplary process for medical imaging according to some embodiments of the present disclosure.

The second imaging controlling unit 416 may be configured to perform process 800 in FIG. 8 to determine, based on image magnification and one or more image quality parameters, one or more first parameters of the detector 112, one or more second parameters of the X-ray generator 113, location information associated with the X-ray generator 113, the detector 112, and the ROI of the scan object. More descriptions regarding the second imaging controlling unit

Figure 6:
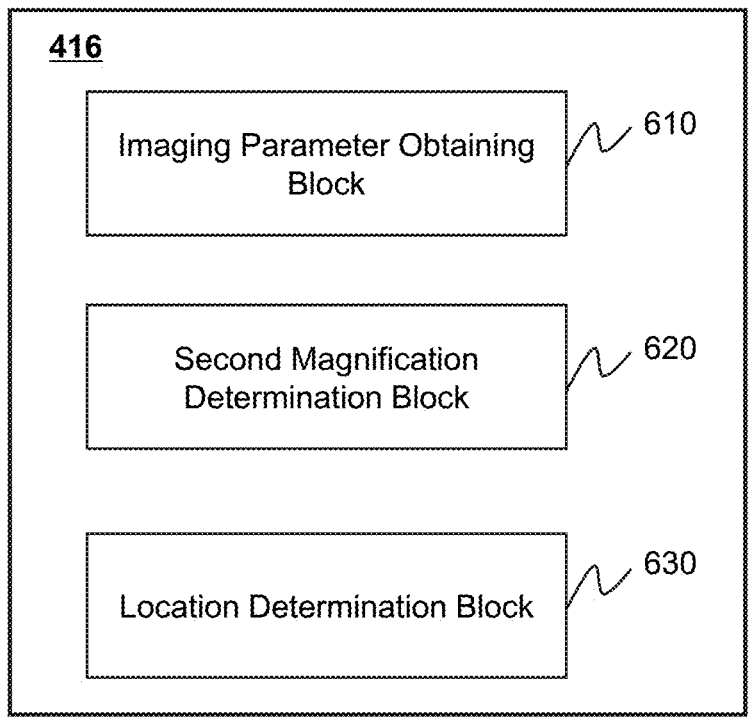
FIG. 6 is a block diagram illustrating an exemplary second imaging controlling unit according to some embodiments of the present disclosure.

416 may be found elsewhere in the present disclosure (e.g., the description in connection with FIG. 6 and/or the process 800 in FIG. 8).

The second controlling module 420 may be configured to adjust one or more exposure parameters of the imaging device 110 to generate an image satisfying target brightness. The second controlling module 420 may include an acquisition unit 422, an equivalent thickness determination unit 424, an exposure parameter determination unit 426, and a scanning unit 428.

The acquisition unit 422 may be configured to obtain an initial image that is captured by scanning a scan object (e.g., the ROI 1102 in FIG. 12) based on one or more initial exposure parameters using an imaging device (e.g., the imaging device 110 in FIG. 1).

In some embodiments, the acquisition unit 422 may obtain the initial image from a storage medium (e.g., the storage device 150, and/or the storage 220) of the imaging system 100. In some embodiments, the acquisition unit 422 may obtain the initial image in real time during a scan process. For example, a plurality of images have been generated during a scan process of scanning the scan object. The initial image may be any one of the plurality of images, such as the first image or the last image.

In some embodiments, the acquisition unit 422 may determine the brightness of the initial image. As used herein, the brightness of an image may refer to an average value of gray values of pixels in at least a portion (e.g., a region of interest) of the image.

The exposure parameters of the imaging device 110 may include a tube voltage of the X-ray generator 113, a tube current of the X-ray generator 113, a filtration mode, a beam field size, a radiation time, a source image distance (SID), or the like, or any combination thereof. The tube voltage refers to a voltage between a cathode of the X-ray generator 113 and an anode of the X-ray generator 113 during the X-ray generator 113 is emitting X-ray beams. The tube current refers to a current between the cathode of the X-ray generator 113 and the anode of the X-ray generator 113 during the X-ray generator 113 is emitting X-ray beams. The filtration mode may include a filter material placed in front of the X-ray generator 113 in order to reduce the intensity of particular X-ray wavelengths from its spectrum and selectively alter the distribution of X-ray wavelengths within a given x-ray beam. Exemplary filter materials may include aluminum, copper, silver, iron, and so on. For filters of different filter materials, the thickness of the filters may be different, which causes different doses of the X-rays transmitted through the filters. The beam field size may be a variable parameter. If the beam field size is relatively large, the generated image may have relatively rich image details, but a relatively poor image resolution. If the beam field size is relatively small, the generated image may have relatively little image details, but a relatively high image resolution.

In some embodiments, the imaging device 110 may scan the scan object under the one or more initial exposure parameters to generate the initial image. For example, if the initial image is the first image during a scan process, the one or more initial exposure parameters may be assigned default values of the imaging system 100 or be preset by a user (e.g., an operator, a doctor, or an imaging technician) of the imaging system 100 through, for example, the I/O 230 and/or the I/O 350.

In some embodiments, if the brightness of the initial image does not satisfy target brightness, the second controlling module 420 may perform an iteration process including one or more iterations until an image of which brightness satisfies the target brightness is generated. For example, each iteration may include operations 920-950 in FIG. 9.

The equivalent thickness determination unit 424 may be configured to determine an equivalent thickness associated with the scan object based on brightness of a first image and the target brightness using a thickness model. The first image may be the initial image in a first iteration of the one or more iterations or an image acquired in a previous iteration. The first image may be generated by scanning the scan object based on one or more first exposure parameters using the imaging device 110. For example, if the first image is the initial image in the first iteration of the one or more iterations of the iteration process, the one or more first exposure parameters may be the one or more initial exposure parameters.

In some embodiments, the thickness model may indicate a relationship among a thickness of a sample (e.g., a water phantom, a polymethyl methacrylate (PMMA) phantom) having X-ray attenuation similar to a human body, the one or more exposure parameters, and brightness of an image generated by scanning the sample corresponding to the thickness under the one or more exposure parameters using the imaging device 110. The thickness model may be take the form of a table, an equation, a machine learning model, or the like, or any combination thereof.

In some embodiments, the equivalent thickness determination unit 424 may determine a ratio of the brightness of the first image to target brightness. For example, if the brightness of the first image is 50 and the target brightness is 100, the ratio is 0.5 (i.e., 50/100). Alternatively, the equivalent thickness determination unit 424 may determine a ratio of the target brightness to the brightness of the first image. For example, if the brightness of the first image is 50 and the target brightness is 100, the ratio is 2 (i.e., 100/50). The equivalent thickness determination unit 424 may determine an equivalent thickness based on the ratio and a reference thickness corresponding to the target brightness and the one or more first exposure parameters using the thickness model.

The exposure parameter determination unit 426 may be configured to determine one or more second exposure parameters corresponding to the equivalent thickness and the target brightness based on the thickness model.

The scanning unit 428 may be configured to generate a second image by directing the imaging device 110 to scan the scan object based on the one or more second exposure parameters.

The scanning unit 428 may be further configured to determine whether the brightness of the second image satisfies the target brightness. In response to a determination that the brightness of the second image satisfies (e.g., the brightness of the second image is equal to the target brightness, or the difference between the brightness of the second image and the target brightness is less than a brightness threshold, such as 0.1) the target brightness, the scanning unit 428 may terminate the iteration process. In response to a determination that the brightness of the second image does not satisfy the target brightness, the scanning unit 428 may initiate a new iteration by repeating operations 920-950 in FIG. 9. In some embodiments, an iteration count of the iteration process may be lower than or equal to 5.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 4). The storage module may be configured to store data generated during any process performed by any component of in the processing device 140. As another example, each of components of the processing device 140 may include a storage device. Additionally or alternatively, the components of the processing device 140 may share a common storage device. As still a further example, the first imaging controlling unit 414 and the second imaging controlling unit 416 may be a same unit that may determine at least one of one or more first parameters of the detector 112, one or more second parameters of the X-ray generator 113, location information associated with the X-ray generator 113, the detector 112, or the ROI of the scan object, wherein the determination may be performed based on at least one of location information associated with the X-ray generator 113, the detector 112, the ROI of the scan object, image magnification, or one or more image quality parameters. As still a further example, the first controlling module 410 or the second controlling module 420 may be omitted.

Figure 5:
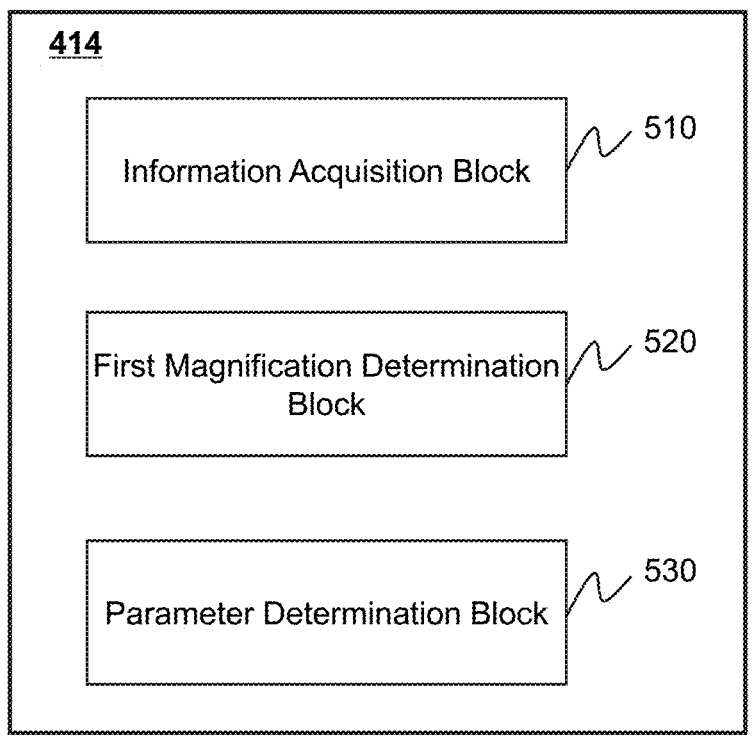
FIG. 5 is a block diagram illustrating an exemplary first imaging controlling unit according to some embodiments of the present disclosure.

FIG. 5 is a block diagram illustrating an exemplary first imaging controlling unit according to some embodiments of the present disclosure. The first imaging controlling unit 414 may include an information acquisition block 510, a first magnification determination block 520, and a parameter determination block 530. In some embodiments, at least a portion of the first imaging controlling unit 414 may be implemented on the computing device 200 as illustrated in FIG. 2 or the mobile device 300 as illustrated in FIG. 3.

The information acquisition block 510 may be configured to obtain location information associated with an X-ray generator of an imaging device (e.g., the X-ray generator 113 of the imaging device 110 in FIG. 1), a detector of the imaging device (e.g., the detector 112 of the imaging device 110 in FIG. 1), and a region of interest (ROI) of a scan object.

In some embodiments, the location information associated with the X-ray generator 113, the detector 112, and the ROI may include a source image distance (SID), a source object distance (SOD), an image object distance (IOD), coordinates of the focal spot of the X-ray generator 113 in a coordinate system, coordinates of the center of an imaging region in the detector 112 in the coordinate system, coordinates of the center of the ROI in the coordinate system, or the like, or any combination thereof.

Figure 11:
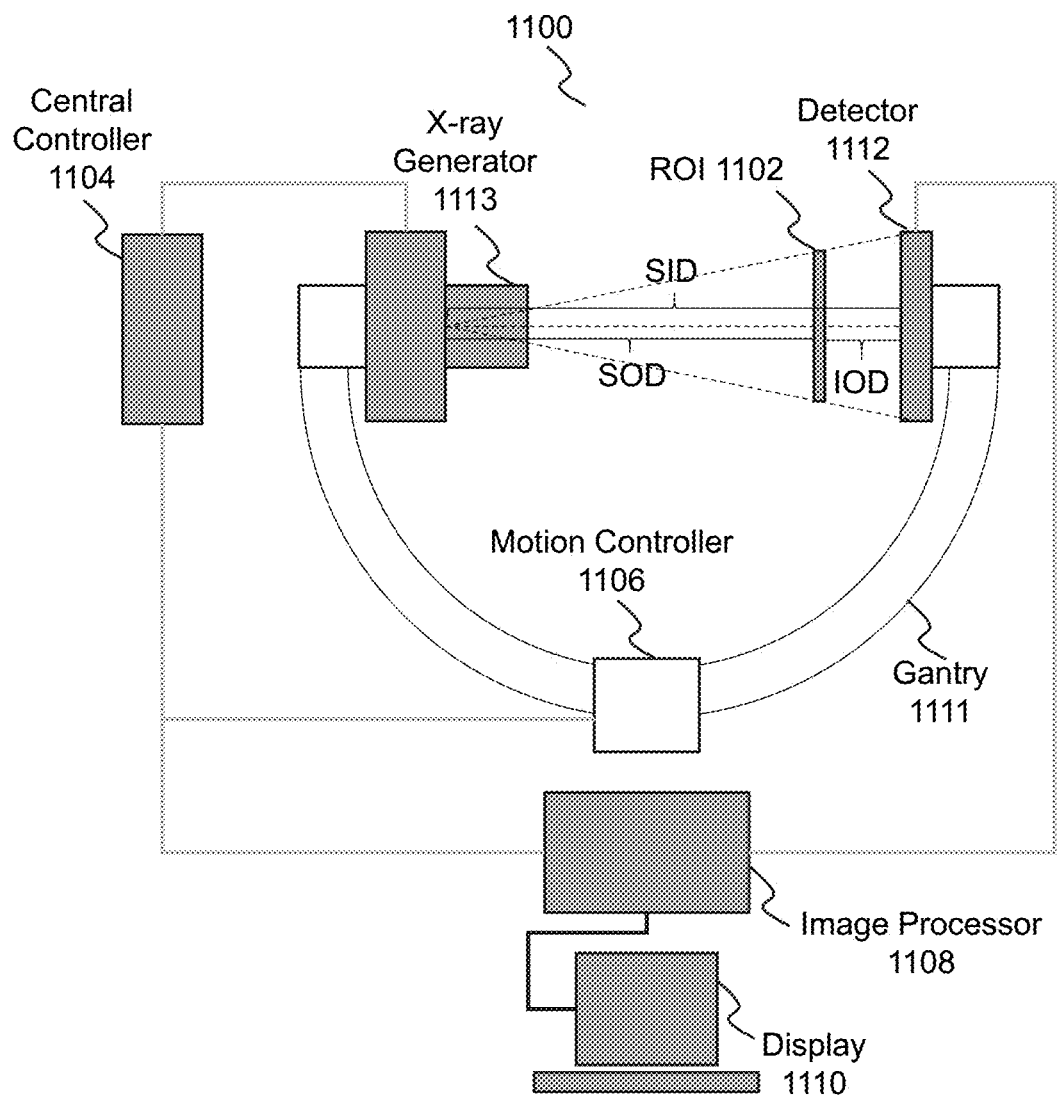
FIG. 11 is a schematic diagram illustrating an exemplary imaging device according to some embodiments of the present disclosure.

The SID refers to a distance between the focal spot of the X-ray generator 113 and the detector 112 (e.g., an imaging region of the detector 112). The SOD refers to a distance between the focal spot of the X-ray generator 113 and the ROI (e.g., the ROI 1102 as illustrated in FIG. 11) of the scan object. The IOD refers to a distance between the ROI (e.g., the ROI 1102 as illustrated in FIG. 11) of the scan object and the detector 112 (e.g., an imaging region of the detector 112). In some embodiments, the SID may be equal to a sum of the SOD and IOD, and the focal spot of the X-ray generator 113, the center of the imaging region of the detector 112, and the center of the ROI of the scan object may be in a straight line.

In some embodiments, the SOD may be determined based on the distance between the coordinates of the focal spot of the X-ray generator 113 and the center of the ROI. The IOD may be determined based on the distance between the coordinates of the center of the ROI and the center of the imaging region in the detector 112. The SID may be determined based on the distance between the coordinates of the focal spot of the X-ray generator 113 and the center of the imaging region in the detector 112.

In some embodiments, if the gantry 111 of the imaging device 110 is an integrated structure, for example, the distance (e.g., the SID) between the X-ray generator 113 and the detector 112 is a constant value, and the X-ray generator 113 is static relative to the detector 112, the information acquisition block 510 may obtain any one of the SOD and the IOD to determine the location information associated with the X-ray generator 113, the detector 112, and the ROI of the scan object. Alternatively or additionally, the information acquisition block 510 may obtain the coordinates of the center of the ROI and any one set of the coordinates of the focal spot of the X-ray generator 113 and the coordinates of the center of the imaging region in the detector 112 to determine the location information associated with the X-ray generator 113, the detector 112, and the ROI of the scan object. In some embodiments, if the gantry 111 of the imaging device 110 (e.g., the gantry of the DR X-ray system) is a structure of which a part supporting the X-ray generator 113 separates from another part supporting the detector 112 such that, for example, the distance (e.g., the SID) between the X-ray generator 113 and the detector 112 may change, the information acquisition block 510 may obtain at least two of the SID, the SOD, and the IOD to determine the location information associated with the X-ray generator 113, the detector 112, and the ROI of the scan object. Alternatively or additionally, the information acquisition block 510 may obtain the coordinates of the center of the ROI, the coordinates of the focal spot of the X-ray generator 113, and the coordinates of the center of the imaging region in the detector 112 to determine the location information associated with the X-ray generator 113, the detector 112, and the ROI of the scan object.

The first magnification determination block 520 may be configured to determine image magnification based on the location information. In some embodiments, the higher the image magnification is, the clearer details of the image may be. In some embodiments, the first magnification determination block 520 may determine the image magnification by dividing the SID by the SOD (e.g., SID/SOD).

The parameter determination block 530 may be configured to determine one or more first parameters of the detector 112 and one or more second parameters of the X-ray generator 113 based on the image magnification, and generate an image of the image magnification by directing the imaging device 110 to scan the ROI based on the one or more first parameters of the detector 112 and the one or more second parameters of the X-ray generator 113.

In some embodiments, the one or more first parameters of the detector 112 may include a pixel size, an image readout mode (e.g., a binning mode), an integration time, a frame rate, X-ray dose on the detector 112, or the like, or any combination thereof. In the binning mode, electrical charges of two or more detector units that are adjacent to each other in the detector 112 may be read out as one pixel in an image. The one or more second parameters of the X-ray generator 113 may include a focal spot size, a pulse frequency, a pulse width, a radiation power, a tube voltage, a tube current, a radiation time, or the like, or any combination thereof.

In some embodiments, the one or more first parameters of the detector 112 may be different from the one or more first preset parameters of the detector 112, and the one or more second parameters of the X-ray generator 113 may be different from the one or more second preset parameters of the X-ray generator 113. After determining the one or more first parameters of the detector 112 and the one or more second parameters of the X-ray generator 113, the parameter determination block 530 may adjust the detector 112 from a first configuration specified by the one or more first preset parameters to a second configuration specified by the one or more first parameters, adjust the X-ray generator 113 from a first configuration specified by the one or more second preset parameters to a second configuration specified by the one or more second parameters, and generate an image of the image magnification by directing the imaging device 110 to scan the ROI using the detector 112 under the second configuration specified by the one or more first parameters and the X-ray generator 113 under the second configuration specified by the one or more second parameters.

In some embodiments, the parameter determination block 530 may determine the one or more first parameters of the detector 112 and the one or more second parameters of the X-ray generator 113 based on the image magnification and one or more image quality parameters. The one or more image quality parameters may include an image contrast, an image resolution, target brightness, or the like, or any combination thereof. In some embodiments, a user (e.g., an operator, a doctor, or an imaging technician) of the imaging system 100 may input the one or more image quality parameters through, for example, the I/O 230 and/or the I/O 350. The one or more image quality parameters may be stored in a storage medium (e.g., the storage device 150, and/or the storage 220) of the imaging system 100. The parameter determination block 530 may obtain the one or more image quality parameters from the storage medium. In some embodiments, an image that satisfies the one or more image quality parameters and the image magnification may be generated by scanning the ROI using the imaging device 110 whose detector 112 is under a configuration specified by the one or more first parameters and whose X-ray generator 113 is under a configuration specified by the one or more second parameters.

In some embodiments, the one or more first parameters of the detector 112 and the one or more second parameters of the X-ray generator 113 may be determined by modifying at least one of the one or more first preset parameters of the detector 112 and the one or more second preset parameters of the X-ray generator 113 manually, automatically, or semi-automatically based on user experience.

In some embodiments, the parameter determination block 530 may determine the one or more first parameters of the detector 112 and the one or more second parameters of the X-ray generator 113 based on the one or more image quality parameters and the image magnification by querying a first parameter table. The first parameter table may include a relationship among the image magnification, the one or more image quality parameters, the one or more first parameters of the detector 112, and the one or more second parameters of the X-ray generator 113. The first parameter table may be stored in a storage medium (e.g., the storage device 150, and/or the storage 220) of the imaging system 100. The parameter determination block 530 may obtain the first parameter table from the storage medium.

In some embodiments, the parameter determination block 530 may determine the one or more first parameters of the detector 112 and the one or more second parameters of the X-ray generator 113 based on a first parameter estimation model. The parameter determination block 530 may input the image magnification and the one or more image quality parameters into the first parameter estimation model. The first parameter estimation model may estimate the one or more first parameters of the detector 112 and one or more second parameters of the X-ray generator 113 based on the image magnification and the one or more image quality parameters. Exemplary first parameter estimation models may include convolutional neural networks (CNNs), artificial neural networks (ANNs), recurrent neural networks (RNNs), deep neural networks, or the like, or any combination thereof. The first parameter estimation model may be stored in a storage medium (e.g., the storage device 150, and/or the storage 220) of the imaging system 100. The parameter determination block 530 may obtain the first parameter estimation model from the storage medium.

Merely by way of example, the parameter determination block 530 may determine the pixel size of the detector 112 and the focal size of the X-ray generator 113 based on the one or more quality image parameters and the image magnification, and determine the X-ray dose on the detector 112 based on the pixel size of the detector 112 and the focal size of the X-ray generator 113. In some embodiments, the more the one or more first parameters and the one or more second parameters, the higher the accuracy of the image generated by the imaging device 110, which is useful for diagnosis.

In some embodiments, because information associated with a target (e.g., a lesion) in the ROI may affect the determination of the one or more first parameters of the detector 112 and the one or more second parameters of the X-ray generator 113, the parameter determination block 530 may also obtain the information associated with the target in the ROI. The information associated with the target in the ROI may include a composition of the target, X-ray attenuation through the target, or the like, or any combination thereof. The parameter determination block 530 may determine the one or more first parameters of the detector 112 and the one or more second parameters of the X-ray generator 113 based on the image magnification, the one or more image quality parameters, and the information associated with the target. For example, if the target includes relatively more bony tissue of which the X-ray attenuation is relatively high, a relatively higher tube voltage may be used to generate an image satisfying target brightness. As another example, if the target includes relatively more adipose tissue of which the X-ray attenuation is relatively low, a relatively lower tube voltage may be used to generate an image satisfying the same target brightness.

In some embodiments, the parameter determination block 530 may obtain the information associated with the target in the ROI by directing the imaging device 110 to scan the ROI under the location information associated with the detector 112, the X-ray generator 113, and the ROI, the one or more first preset parameters, and the one or more second preset parameters to generate an image of the target. The parameter determination block 530 may obtain the information associated with the target in the ROI by processing the image, such as edge segmentation. Exemplary edge segmentation techniques may include Sobel edge segmentation, Prewitt edge segmentation, Krisch edge segmentation, or the like, or any combination thereof.

In some embodiments, the parameter determination block 530 may obtain the information associated with the target in the ROI based on a scan protocol. The scan protocol may include a composition of the target, the X-ray attenuation through the target, a scan time, the location information associated with the detector 112, the X-ray generator 113, and the ROI, the one or more first preset parameters of the detector 112, the one or more second preset parameters of the X-ray generator 113, the one or more image quality parameters, or the like, or any combination thereof.

It should be noted that the above description of the first imaging controlling unit 414 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the parameter determination block 530 may be divided into two sub-blocks. One of the two sub-blocks may be configured to determine the one or more first parameters of the detector 112 and the one or more second parameters of the X-ray generator 113 based on the image magnification and the one or more image quality parameters. The other one sub-block may be configured to generate an image of the image magnification by directing the imaging device 110 to scan the ROI based on the one or more first parameters of the detector 112 and the one or more second parameters of the X-ray generator 113.

FIG. 6 is a block diagram illustrating an exemplary second imaging controlling unit according to some embodiments of the present disclosure. The second imaging controlling unit 416 may include an imaging parameter obtaining block 610, a second magnification determination block 620, and a location determination block 630. In some embodiments, at least a portion of the second imaging controlling unit 416 may be implemented on the computing device 200 as illustrated in FIG. 2 or the mobile device 300 as illustrated in FIG. 3.

The imaging parameter obtaining block 610 may be configured to determine one or more first parameters of a detector of an imaging device (e.g., the detector 112 of the imaging device 110) and one or more second parameters of an X-ray generator of the imaging device (e.g., the X-ray generator 113 of the imaging device 110) based on one or more image quality parameters.

In some embodiments, the one or more first parameters of the detector 112 may be different from the one or more first preset parameters of the detector 112, and the one or more second parameters of the X-ray generator 113 may be different from the one or more second preset parameters of the X-ray generator 113. After determining the one or more first parameters of the detector 112 and the one or more second parameters of the X-ray generator 113, the imaging parameter obtaining block 610 may adjust the detector 112 from a first configuration specified by the one or more first preset parameters to a second configuration specified by the one or more first parameters, and adjust the X-ray generator 113 from a first configuration specified by the one or more second preset parameters to a second configuration specified by the one or more second parameters.

In some embodiments, the one or more first parameters of the detector 112 may include a pixel size, an image readout mode (e.g., a binning mode), an integration time, a frame rate, X-ray dose on the detector, or the like, or any combination thereof. In the binning mode, electrical charges of two or more detector units that are adjacent to each other in the detector 112 may be read out as one pixel in an image. The one or more second parameters of the X-ray generator 113 may include a focal spot size, a pulse frequency, a pulse width, a radiation power, a tube voltage, a tube current, a radiation time, or the like, or any combination thereof.

In some embodiments, the one or more image quality parameters may include an image contrast, an image resolution, target brightness, or the like, or any combination thereof. In some embodiments, a user (e.g., an operator, a doctor, or an imaging technician) of the imaging system 100 may preset the one or more image quality parameters through, for example, the I/O 230 and/or the I/O 350. The one or more image quality parameters may be stored in a storage medium (e.g., the storage device 150, and/or the storage 220) of the imaging system 100. The imaging parameter obtaining block 610 may obtain the one or more image quality parameters from the storage medium.

In some embodiments, the one or more first parameters of the detector 112 and the one or more second parameters of the X-ray generator 113 may be determined by modifying at least one of the one or more first preset parameters of the detector 112 and the one or more second preset parameters of the X-ray generator 113 manually, automatically, or semi-automatically based on user experience.

In some embodiments, the imaging parameter obtaining block 610 may determine the one or more first parameters of the detector 112 and the one or more second parameters of the X-ray generator 113 based on the one or more image quality parameters by querying a second parameter table. The second parameter table may include a relationship among the one or more image quality parameters, the one or more first parameters of the detector 112, and the one or more second parameters of the X-ray generator 113. The second parameter table may be stored in a storage medium (e.g., the storage device 150, and/or the storage 220) of the imaging system 100. The imaging parameter obtaining block 610 may obtain the second parameter table from the storage medium.

In some embodiments, the imaging parameter obtaining block 610 may determine the one or more first parameters of the detector 112 and the one or more second parameters of the X-ray generator 113 based on a second parameter estimation model. The imaging parameter obtaining block 610 may input the one or more image quality parameters into the second parameter estimation model. The second parameter estimation model may estimate the one or more first parameters of the detector 112 and one or more second parameters of the X-ray generator 113 based on the one or more image quality parameters. Exemplary second parameter estimation models may include convolutional neural networks (CNNs), artificial neural networks (ANNs), recurrent neural networks (RNNs), deep neural networks, or the like, or any combination thereof. The second parameter estimation model may be stored in a storage medium (e.g., the storage device 150, and/or the storage 220) of the imaging system 100. The first controlling module 410 may obtain the second parameter estimation model from the storage medium.

Merely by way of example, the imaging parameter obtaining block 610 may determine the pixel size of the detector 112 and the focal size of the X-ray generator 113 based on the one or more quality image parameters, and determine the X-ray dose on the detector 112 based on the pixel size of the detector 112 and the focal size of the X-ray generator 113. In some embodiments, the more the one or more first parameters and the one or more second parameters, the higher the accuracy of the image generated by the imaging device 110, which is useful for diagnosis.

The second magnification determination block 620 may be configured to determine image magnification based on the one or more first parameters of the detector 112 and the one or more second parameters of the X-ray generator 113. In some embodiments, the higher the image magnification is, the clearer details of the image may be.

In some embodiments, the image magnification may be determined based on user experience.

In some embodiments, the second magnification determination block 620 may determine the image magnification based on the one or more first parameters and the one or more second parameters by querying a third parameter table. The third parameter table may include a relationship among the image magnification, the one or more first parameters of the detector 112, and the one or more second parameters of the X-ray generator 113. The third parameter table may be stored in a storage medium (e.g., the storage device 150, and/or the storage 220) of the imaging system 100. The second magnification determination block 620 may obtain the third parameter table from the storage medium.

In some embodiments, the second magnification determination block 620 may determine the one or more first parameters of the detector 112 and the one or more second parameters of the X-ray generator 113 based on a third parameter estimation model. The second magnification determination block 620 may input the one or more first parameters of the detector 112 and one or more second parameters of the X-ray generator 113 into the third parameter estimation model. The third parameter estimation model may estimate the one or more first parameters of the detector 112 and one or more second parameters of the X-ray generator 113 based on the image magnification. Exemplary third parameter estimation models may include convolutional neural networks (CNNs), artificial neural networks (ANNs), recurrent neural networks (RNNs), deep neural networks, or the like, or any combination thereof. The third parameter estimation model may be stored in a storage medium (e.g., the storage device 150, and/or the storage 220) of the imaging system 100. The second magnification determination block 620 may obtain the third parameter estimation model from the storage medium.

The location determination block 630 may be configured to adjust locations of the X-ray generator 113, the detector 112, or the ROI based on the image magnification.

In some embodiments, the location determination block 630 may determine location information associated with the X-ray generator 113, the detector 112, and the ROI based on the image magnification and adjust the locations of the X-ray generator 113, the detector 112, or the ROI based on the location information.

In some embodiments, the location information associated with the X-ray generator 113, the detector 112, and the ROI may include a source image distance (SID), a source object distance (SOD), an image object distance (IOD), coordinates of the focal spot of the X-ray generator 113 in a coordinate system, coordinates of the center of an imaging region in the detector 112 in the coordinate system, coordinates of the center of the ROI in the coordinate system, or the like, or any combination thereof.

The SID refers to a distance between the focal spot of the X-ray generator 113 and the detector 112 (e.g., an imaging region of the detector 112). The SOD refers to a distance between the focal spot of the X-ray generator 113 and the ROI (e.g., the ROI 1102 as illustrated in FIG. 11) of the scan object. The IOD refers to a distance between the ROI (e.g., the ROI 1102 as illustrated in FIG. 11) of the scan object and the detector 112 (e.g., an imaging region of the detector 112). In some embodiments, the SID may be equal to a sum of the SOD and IOD, and the focal spot of the X-ray generator 113, the center of the imaging region of the detector 112, and the center of the ROI of the scan object may be in a straight line.

In some embodiments, the SOD may be determined based on the distance between the coordinates of the focal spot of the X-ray generator 113 and the center of the ROI. The IOD may be determined based on the distance between the coordinates of the center of the ROI and the center of the imaging region in the detector 112. The SID may be determined based on the distance between the coordinates of the focal spot of the X-ray generator 113 and the center of the imaging region in the detector 112.

In some embodiments, the image magnification may be determined by dividing the SID by the SOD (e.g., SID/SOD).

In some embodiments, if the gantry 111 of the imaging device 110 is an integrated structure, for example, the distance (e.g., the SID) between the X-ray generator 113 and the detector 112 is a constant value, and the X-ray generator 113 is static relative to the detector 112, the location determination block 630 may determine the location information based on the image magnification.

In some embodiments, if the gantry 111 of the imaging device 110 (e.g., the gantry of the DR X-ray system) is a structure of which a part supporting the X-ray generator 113 separates from another part supporting the detector 112 such that, for example, the distance (e.g., the SID) between the X-ray generator 113 and the detector 112 may change, the location determination block 630 may determine the location information based on the image magnification and the one or more image quality parameters.

For example, the locations of the detector 112, the X-ray generator 113, or the ROI may be adjusted manually, automatically, or semi-automatically based on user experience.

As another example, the location determination block 630 may determine the location information based on the one or more image quality parameters and the image magnification by querying a fourth parameter table. The fourth parameter table may include a relationship among the location information, the image magnification, and the one or more image quality parameters. The fourth parameter table may be stored in a storage medium (e.g., the storage device 150, and/or the storage 220) of the imaging system 100. The location determination block 630 may obtain the fourth parameter table from the storage medium.

As still another example, the location determination block 630 may determine the location information based on a fourth parameter estimation model. The location determination block 630 may input the image magnification and the one or more image quality parameters into the fourth parameter estimation model. The fourth parameter estimation model may estimate the location information based on the image magnification and the one or more image quality parameters. Exemplary fourth parameter estimation models may include convolutional neural networks (CNNs), artificial neural networks (ANNs), recurrent neural networks (RNNs), deep neural networks, or the like, or any combination thereof. For those skilled in the art, the process for training the model may be found in prior art, and not be described in detail. The fourth parameter estimation model may be stored in a storage medium (e.g., the storage device 150, and/or the storage 220) of the imaging system 100. The location determination block 630 may obtain the fourth parameter estimation model from the storage medium.

In some embodiments, the location determination block 630 may obtain, from a storage medium (e.g., the storage device 150, and/or the storage 220) of the imaging system 100, a fifth parameter table including a relationship among the location information, the image magnification, the one or more image quality parameters, the one or more first parameters of the detector 112, and the one or more second parameters of the X-ray generator 113. The location determination block 630 may determine the one or more first parameters of the detector 112, the one or more second parameters of the X-ray generator 113, the image magnification, and the location information based on the one or more image quality parameters using the fifth parameter table.

In some embodiments, the location determination block 630 may obtain, from a storage medium (e.g., the storage device 150, and/or the storage 220) of the imaging system 100, a fifth parameter estimation model. The location determination block 630 may input the one or more image quality parameters into the fifth parameter estimation model. The fifth parameter estimation model may estimate the one or more first parameters of the detector 112, the one or more second parameters of the X-ray generator 113, the image magnification, and the location information based on the one or more image quality parameters. Exemplary fifth parameter estimation models may include convolutional neural networks (CNNs), artificial neural networks (ANNs), recurrent neural networks (RNNs), deep neural networks, or the like, or any combination thereof.

After adjusting the locations of the X-ray generator 113, the detector 112, or the ROI, the location determination block 630 may direct the imaging device 110 to scan the ROI under the location information, the second configuration specified by the one or more first parameters, and the second configuration specified by the one or more second parameters to generate an image that satisfies the image magnification and the one or more image quality parameters.

It should be noted that the above description of the second imaging controlling unit 416 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the location determination block 630 may be divided into two sub-blocks. One of the two sub-blocks may be configured to determine the location information based on the image magnification. The other one sub-block may be configured to generate an image of the image magnification by directing the imaging device 110 to scan the ROI based on the location information, the one or more first parameters of the detector 112, and the one or more second parameters of the X-ray generator 113.

In some embodiments, a doctor needs images having different image magnification in different application scenarios. For example, a doctor needs an image having a relatively higher image magnification if the doctor wants to observe more details of an ROI of a scan object, such as a finger fracture or a lesion in the mouth of the scan object. As another example, a doctor needs an image having a relatively larger field of view (FOV) if the doctor wants to observe a surgical wound after a surgery. In this case, an image having a relatively smaller image magnification may be needed. In some embodiments, the detector 112 may be set based on one or more first preset parameters of the detector 112, and the X-ray generator 113 may be set based on one or more second preset parameters of the X-ray generator 113. However, it is hard to generate images that have different image magnification and satisfy predetermined image quality under the one or more first preset parameters and the one or more second preset parameters. Therefore, the processing device 140 (e.g., the first controlling module 410) may perform process 700 in FIG. 7 and/or process 800 in FIG. 8 to adjust the parameters of the detector 112 and the X-ray generator 113 to generate images that have different image magnification and satisfy the predetermined image quality.

FIG. 7 is a flowchart illustrating an exemplary process for medical imaging according to some embodiments of the present disclosure. In some embodiments, one or more operations of the process 700 illustrated in FIG. 7 for medical imaging may be implemented in the imaging system 100 illustrated in FIG. 1. For example, the process 700 illustrated in FIG. 7 may be stored in a storage medium (e.g., the storage device 150, and/or the storage 220) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules/units/blocks of the processing device 140 illustrated in FIGS. 4-6). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 710, the first controlling module 410 (e.g., the first imaging controlling unit 414, and/or the information acquisition block 510) may obtain location information associated with an X-ray generator of an imaging device (e.g., the X-ray generator 113 of the imaging device 110 in FIG. 1), a detector of the imaging device (e.g., the detector 112 of the imaging device 110 in FIG. 1), and a region of interest (ROI) of a scan object.

In some embodiments, the location information associated with the X-ray generator 113, the detector 112, and the ROI may include a source image distance (SID), a source object distance (SOD), an image object distance (IOD), coordinates of the focal spot of the X-ray generator 113 in a coordinate system, coordinates of the center of an imaging region in the detector 112 in the coordinate system, coordinates of the center of the ROI in the coordinate system, or the like, or any combination thereof.

The SID (as exemplified in FIG. 11) refers to a distance between the focal spot of the X-ray generator 113 and the detector 112 (e.g., an imaging region of the detector 112). The SOD (as exemplified in FIG. 11) refers to a distance between the focal spot of the X-ray generator 113 and the ROI (e.g., the ROI 1102 as illustrated in FIG. 11) of the scan object. The IOD (as exemplified in FIG. 11) refers to a distance between the ROI (e.g., the ROI 1102 as illustrated in FIG. 11) of the scan object and the detector 112 (e.g., an imaging region of the detector 112). In some embodiments, the SID may be equal to a sum of the SOD and IOD, and the focal spot of the X-ray generator 113, the center of the imaging region of the detector 112, and the center of the ROI of the scan object may be in a straight line.

In some embodiments, the SOD may be determined based on the distance between the coordinates of the focal spot of the X-ray generator 113 and the center of the ROI. The IOD may be determined based on the distance between the coordinates of the center of the ROI and the center of the imaging region in the detector 112. The SID may be determined based on the distance between the coordinates of the focal spot of the X-ray generator 113 and the center of the imaging region in the detector 112.

In some embodiments, if the gantry 111 of the imaging device 110 is an integrated structure, for example, the distance (e.g., the SID) between the X-ray generator 113 and the detector 112 is a constant value, and the X-ray generator 113 is static relative to the detector 112, the first controlling module 410 may obtain any one of the SOD and the IOD to determine the location information associated with the X-ray generator 113, the detector 112, and the ROI of the scan object. Alternatively or additionally, the first controlling module 410 may obtain the coordinates of the center of the ROI and any one set of the coordinates of the focal spot of the X-ray generator 113 and the coordinates of the center of the imaging region in the detector 112 to determine the location information associated with the X-ray generator 113, the detector 112, and the ROI of the scan object. In some embodiments, if the gantry 111 of the imaging device 110 (e.g., the gantry of the DR X-ray system) is a structure of which a part supporting the X-ray generator 113 separates from another part supporting the detector 112 such that, for example, the distance (e.g., the SID) between the X-ray generator 113 and the detector 112 may change, the first controlling module 410 may obtain at least two of the SID, the SOD, and the IOD to determine the location information associated with the X-ray generator 113, the detector 112, and the ROI of the scan object. Alternatively or additionally, the first controlling module 410 may obtain the coordinates of the center of the ROI, the coordinates of the focal spot of the X-ray generator 113, and the coordinates of the center of the imaging region in the detector 112 to determine the location information associated with the X-ray generator 113, the detector 112, and the ROI of the scan object.

In some embodiments, a user (e.g., a doctor, an imaging technician, or an operator) of the imaging system 100 may input through, for example, the I/O 230 in FIG. 2 or the I/O 350 in FIG. 3, the location information. A motion controller (e.g., a motion controller 1106 in FIG. 11) may drive the detector 112, the X-ray generator 113, or the ROI (e.g., the scanning table 114) to corresponding locations based on the input location information.

In some embodiments, the user of the imaging system 100 may manually place the detector 112, the X-ray generator 113, or the ROI (e.g., the scanning table 114) to desired locations. The imaging device 110 may record the location information and transmit the location information to the processing device 140 (e.g., the first controlling module 410).

In 720, the first controlling module 410 (e.g., the first imaging controlling unit 414, and/or the first magnification determination block 520) may determine image magnification based on the location information. In some embodiments, the higher the image magnification is, the clearer details of the image may be. In some embodiments, the first controlling module 410 may determine the image magnification by dividing the SID by the SOD (e.g., SID/SOD).

In 730, the first controlling module 410 (e.g., the first imaging controlling unit 414, and/or the parameter determination block 530) may determine one or more first parameters of the detector 112 and one or more second parameters of the X-ray generator 113 based on the image magnification, and generate an image of the image magnification by directing the imaging device 110 to scan the ROI based on the one or more first parameters of the detector 112 and the one or more second parameters of the X-ray generator 113.

In some embodiments, the one or more first parameters of the detector 112 may include a pixel size, an image readout mode (e.g., a binning mode), an integration time, a frame rate, X-ray dose on the detector 112, or the like, or any combination thereof. In the binning mode, electrical charges of two or more detector units that are adjacent to each other in the detector 112 may be read out as one pixel in an image. The one or more second parameters of the X-ray generator 113 may include a focal spot size, a pulse frequency, a pulse width, a radiation power, a tube voltage, a tube current, a radiation time, or the like, or any combination thereof.

In some embodiments, the one or more first parameters of the detector 112 may be different from the one or more first preset parameters of the detector 112, and the one or more second parameters of the X-ray generator 113 may be different from the one or more second preset parameters of the X-ray generator 113. After determining the one or more first parameters of the detector 112 and the one or more second parameters of the X-ray generator 113, the first controlling module 410 may adjust the detector 112 from a first configuration specified by the one or more first preset parameters to a second configuration specified by the one or more first parameters, adjust the X-ray generator 113 from a first configuration specified by the one or more second preset parameters to a second configuration specified by the one or more second parameters, and generate an image of the image magnification by directing the imaging device 110 to scan the ROI using the detector 112 under the second configuration specified by the one or more first parameters and the X-ray generator 113 under the second configuration specified by the one or more second parameters.

In some embodiments, the first controlling module 410 may determine the one or more first parameters of the detector 112 and the one or more second parameters of the X-ray generator 113 based on the image magnification and one or more image quality parameters. The one or more image quality parameters may include an image contrast, an image resolution, target brightness, or the like, or any combination thereof. In some embodiments, a user (e.g., an operator, a doctor, or an imaging technician) of the imaging system 100 may input the one or more image quality parameters through, for example, the I/O 230 and/or the I/O 350. The one or more image quality parameters may be stored in a storage medium (e.g., the storage device 150, and/or the storage 220) of the imaging system 100. The first controlling module 410 may obtain the one or more image quality parameters from the storage medium. In some embodiments, an image that satisfies the one or more image quality parameters and the image magnification may be generated by scanning the ROI using the imaging device 110 whose detector 112 is under a configuration specified by the one or more first parameters and whose X-ray generator 113 is under a configuration specified by the one or more second parameters.

In some embodiments, the one or more first parameters of the detector 112 and the one or more second parameters of the X-ray generator 113 may be determined by modifying at least one of the one or more first preset parameters of the detector 112 and the one or more second preset parameters of the X-ray generator 113 manually, automatically, or semi-automatically based on user experience.

In some embodiments, the first controlling module 410 may determine the one or more first parameters of the detector 112 and the one or more second parameters of the X-ray generator 113 based on the one or more image quality parameters and the image magnification by querying a first parameter table. The first parameter table may include a relationship among the image magnification, the one or more image quality parameters, the one or more first parameters of the detector 112, and the one or more second parameters of the X-ray generator 113. The first parameter table may be stored in a storage medium (e.g., the storage device 150, and/or the storage 220) of the imaging system 100. The first controlling module 410 may obtain the first parameter table from the storage medium.

In some embodiments, the first controlling module 410 may determine the one or more first parameters of the detector 112 and the one or more second parameters of the X-ray generator 113 based on a first parameter estimation model. The first controlling module 410 may input the image magnification and the one or more image quality parameters into the first parameter estimation model. The first parameter estimation model may estimate the one or more first parameters of the detector 112 and one or more second parameters of the X-ray generator 113 based on the image magnification and the one or more image quality parameters. Exemplary first parameter estimation models may include convolutional neural networks (CNNs), artificial neural networks (ANNs), recurrent neural networks (RNNs), deep neural networks, or the like, or any combination thereof. The first parameter estimation model may be stored in a storage medium (e.g., the storage device 150, and/or the storage 220) of the imaging system 100. The first controlling module 410 may obtain the first parameter estimation model from the storage medium.

Merely by way of example, the first controlling module 410 may determine the pixel size of the detector 112 and the focal size of the X-ray generator 113 based on the one or more quality image parameters and the image magnification, and determine the X-ray dose on the detector 112 based on the pixel size of the detector 112 and the focal size of the X-ray generator 113. In some embodiments, the more the one or more first parameters and the one or more second parameters, the higher the accuracy of the image generated by the imaging device 110, which is useful for diagnosis.

In some embodiments, because information associated with a target (e.g., a lesion) in the ROI may affect the determination of the one or more first parameters of the detector 112 and the one or more second parameters of the X-ray generator 113, the first controlling module 410 may also obtain the information associated with the target in the ROI. The information associated with the target in the ROI may include a composition of the target, X-ray attenuation through the target, or the like, or any combination thereof. The first controlling module 410 may determine the one or more first parameters of the detector 112 and the one or more second parameters of the X-ray generator 113 based on the image magnification, the one or more image quality parameters, and the information associated with the target. For example, if the target includes relatively more bony tissue of which the X-ray attenuation is relatively high, a relatively higher tube voltage may be used to generate an image satisfying target brightness. As another example, if the target includes relatively more adipose tissue of which the X-ray attenuation is relatively low, a relatively lower tube voltage may be used to generate an image satisfying the same target brightness.

In some embodiments, the first controlling module 410 may obtain the information associated with the target in the ROI by directing the imaging device 110 to scan the ROI under the location information associated with the detector 112, the X-ray generator 113, and the ROI, the one or more first preset parameters, and the one or more second preset parameters to generate an image of the target. The first controlling module 410 may obtain the information associated with the target in the ROI by processing the image, such as edge segmentation. Exemplary edge segmentation techniques may include Sobel edge segmentation, Prewitt edge segmentation, Krisch edge segmentation, or the like, or any combination thereof.

In some embodiments, the first controlling module 410 may obtain the information associated with the target in the ROI based on a scan protocol. The scan protocol may include a composition of the target, the X-ray attenuation through the target, a scan time, the location information associated with the detector 112, the X-ray generator 113, and the ROI, the one or more first preset parameters of the detector 112, the one or more second preset parameters of the X-ray generator 113, the one or more image quality parameters, or the like, or any combination thereof.

It should be noted that the description of the process 700 is provided for the purposes of illustration, and not intended to limit the scope of the present disclosure. For persons having ordinary skills in the art, various variations and modifications may be conducted under the teaching of the present disclosure. However, those variations and modifications may not depart from the protecting of the present disclosure.

FIG. 8 is a flowchart illustrating an exemplary process for medical imaging according to some embodiments of the present disclosure. In some embodiments, one or more operations of the process 800 illustrated in FIG. 8 for medical imaging may be implemented in the imaging system 100 illustrated in FIG. 1. For example, the process 800 illustrated in FIG. 8 may be stored in a storage medium (e.g., the storage device 150, and/or the storage 220) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules/units/blocks of the processing device 140 illustrated in FIGS. 4-6). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In 810, the first controlling module 410 (e.g., the second imaging controlling unit 416, and/or the imaging parameter obtaining block 610) may determine one or more first parameters of a detector of an imaging device (e.g., the detector 112 of the imaging device 110) and one or more second parameters of an X-ray generator of the imaging device (e.g., the X-ray generator 113 of the imaging device 110) based on one or more image quality parameters.

In some embodiments, the one or more first parameters of the detector 112 may be different from the one or more first preset parameters of the detector 112, and the one or more second parameters of the X-ray generator 113 may be different from the one or more second preset parameters of the X-ray generator 113. After determining the one or more first parameters of the detector 112 and the one or more second parameters of the X-ray generator 113, the first controlling module 410 may adjust the detector 112 from a first configuration specified by the one or more first preset parameters to a second configuration specified by the one or more first parameters, and adjust the X-ray generator 113 from a first configuration specified by the one or more second preset parameters to a second configuration specified by the one or more second parameters.

In some embodiments, the one or more first parameters of the detector 112 may include a pixel size, an image readout mode (e.g., a binning mode), an integration time, a frame rate, X-ray dose on the detector, or the like, or any combination thereof. In the binning mode, electrical charges of two or more detector units that are adjacent to each other in the detector 112 may be read out as one pixel in an image. The one or more second parameters of the X-ray generator 113 may include a focal spot size, a pulse frequency, a pulse width, a radiation power, a tube voltage, a tube current, a radiation time, or the like, or any combination thereof.

In some embodiments, the one or more image quality parameters may include an image contrast, an image resolution, target brightness, or the like, or any combination thereof. In some embodiments, a user (e.g., an operator, a doctor, or an imaging technician) of the imaging system 100 may preset the one or more image quality parameters through, for example, the I/O 230 and/or the I/O 350. The one or more image quality parameters may be stored in a storage medium (e.g., the storage device 150, and/or the storage 220) of the imaging system 100. The first controlling module 410 may obtain the one or more image quality parameters from the storage medium.

In some embodiments, the one or more first parameters of the detector 112 and the one or more second parameters of the X-ray generator 113 may be determined by modifying at least one of the one or more first preset parameters of the detector 112 and the one or more second preset parameters of the X-ray generator 113 manually, automatically, or semi-automatically based on user experience.

In some embodiments, the first controlling module 410 may determine the one or more first parameters of the detector 112 and the one or more second parameters of the X-ray generator 113 based on the one or more image quality parameters by querying a second parameter table. The second parameter table may include a relationship among the one or more image quality parameters, the one or more first parameters of the detector 112, and the one or more second parameters of the X-ray generator 113. The second parameter table may be stored in a storage medium (e.g., the storage device 150, and/or the storage 220) of the imaging system 100. The first controlling module 410 may obtain the second parameter table from the storage medium.

In some embodiments, the first controlling module 410 may determine the one or more first parameters of the detector 112 and the one or more second parameters of the X-ray generator 113 based on a second parameter estimation model. The first controlling module 410 may input the one or more image quality parameters into the second parameter estimation model. The second parameter estimation model may estimate the one or more first parameters of the detector 112 and one or more second parameters of the X-ray generator 113 based on the one or more image quality parameters. Exemplary second parameter estimation models may include convolutional neural networks (CNNs), artificial neural networks (ANNs), recurrent neural networks (RNNs), deep neural networks, or the like, or any combination thereof. The second parameter estimation model may be stored in a storage medium (e.g., the storage device 150, and/or the storage 220) of the imaging system 100. The first controlling module 410 may obtain the second parameter estimation model from the storage medium.

Merely by way of example, the first controlling module 410 may determine the pixel size of the detector 112 and the focal size of the X-ray generator 113 based on the one or more quality image parameters, and determine the X-ray dose on the detector 112 based on the pixel size of the detector 112 and the focal size of the X-ray generator 113. In some embodiments, the more the one or more first parameters and the one or more second parameters, the higher the accuracy of the image generated by the imaging device 110, which is useful for diagnosis.

In 820, the first controlling module 410 (e.g., the second imaging controlling unit 416, and/or the second magnification determination block 620) may determine image magnification based on the one or more first parameters of the detector 112 and the one or more second parameters of the X-ray generator 113. In some embodiments, the higher the image magnification is, the clearer details of the image may be.

In some embodiments, the image magnification may be determined based on user experience.

In some embodiments, the first controlling module 410 may determine the image magnification based on the one or more first parameters and the one or more second parameters by querying a third parameter table. The third parameter table may include a relationship among the image magnification, the one or more first parameters of the detector 112, and the one or more second parameters of the X-ray generator 113. The third parameter table may be stored in a storage medium (e.g., the storage device 150, and/or the storage 220) of the imaging system 100. The first controlling module 410 may obtain the third parameter table from the storage medium.

In some embodiments, the first controlling module 410 may determine the image magnification based on the one or more first parameters of the detector 112 and the one or more second parameters of the X-ray generator 113 using a third parameter estimation model. The first controlling module 410 may input the one or more first parameters of the detector 112 and one or more second parameters of the X-ray generator 113 into the third parameter estimation model. The third parameter estimation model may estimate the image magnification based on the one or more first parameters of the detector 112 and one or more second parameters of the X-ray generator 113. Exemplary third parameter estimation models may include convolutional neural networks (CNNs), artificial neural networks (ANNs), recurrent neural networks (RNNs), deep neural networks, or the like, or any combination thereof. The third parameter estimation model may be stored in a storage medium (e.g., the storage device 150, and/or the storage 220) of the imaging system 100. The first controlling module 410 may obtain the third parameter estimation model from the storage medium.

In 830, the first controlling module 410 (e.g., the second imaging controlling unit 416, and/or the location determination block 630) may adjust locations of the X-ray generator 113, the detector 112, or the ROI based on the image magnification.

In some embodiments, the first controlling module 410 may determine location information associated with the X-ray generator 113, the detector 112, and the ROI based on the image magnification and adjust the locations of the X-ray generator 113, the detector 112, or the ROI based on the location information.

In some embodiments, the location information associated with the X-ray generator 113, the detector 112, and the ROI may include a source image distance (SID), a source object distance (SOD), an image object distance (IOD), coordinates of the focal spot of the X-ray generator 113 in a coordinate system, coordinates of the center of an imaging region in the detector 112 in the coordinate system, coordinates of the center of the ROI in the coordinate system, or the like, or any combination thereof.

The SID (as exemplified in FIG. 11) refers to a distance between the focal spot of the X-ray generator 113 and the detector 112 (e.g., an imaging region of the detector 112). The SOD (as exemplified in FIG. 11) refers to a distance between the focal spot of the X-ray generator 113 and the ROI (e.g., the ROI 1102 as illustrated in FIG. 11) of the scan object. The IOD (as exemplified in FIG. 11) refers to a distance between the ROI (e.g., the ROI 1102 as illustrated in FIG. 11) of the scan object and the detector 112 (e.g., an imaging region of the detector 112). In some embodiments, the SID may be equal to a sum of the SOD and IOD, and the focal spot of the X-ray generator 113, the center of the imaging region of the detector 112, and the center of the ROI of the scan object may be in a straight line.

In some embodiments, the SOD may be determined based on the distance between the coordinates of the focal spot of the X-ray generator 113 and the center of the ROI. The IOD may be determined based on the distance between the coordinates of the center of the ROI and the center of the imaging region in the detector 112. The SID may be determined based on the distance between the coordinates of the focal spot of the X-ray generator 113 and the center of the imaging region in the detector 112.

In some embodiments, the image magnification may be determined by dividing the SID by the SOD (e.g., SID/SOD).

In some embodiments, if the gantry 111 of the imaging device 110 is an integrated structure, for example, as to a C-arm system, the distance (e.g., the SID) between the X-ray generator 113 and the detector 112 may be a constant value in some examples, and thus the X-ray generator 113 may be static relative to the detector 112. The first controlling module 410 may determine the location information based on the image magnification, and adjust the distance between the X-ray generator 113 and the object according to the location information. Usually, the distance between the X-ray generator 113 and the object could be achieved by changing the position of the couch (e.g., the scanning table) on which the patient is supported.

In some embodiments, the imaging device could be an existing DR system. In this system, the gantry of the imaging device (e.g., the gantry of the DR X-ray system) is a structure of which a part supporting the X-ray generator separates from another part supporting the detector, such that, for example, the distance (e.g., the SID) between the X-ray generator and the detector may change, the first controlling module 410 may determine the location information based on the image magnification and the one or more image quality parameters.

For example, the locations of the detector, the X-ray generator, or the ROI may be adjusted manually, automatically, or semi-automatically based on user experience.

As another example, the first controlling module 410 may determine the location information based on the one or more image quality parameters and the image magnification by querying a fourth parameter table. The fourth parameter table may include a relationship among the location information, the image magnification, and the one or more image quality parameters. The fourth parameter table may be stored in a storage medium (e.g., the storage device 150, and/or the storage 220) of the imaging system 100. The first controlling module 410 may obtain the fourth parameter table from the storage medium.

As still another example, the first controlling module 410 may determine the location information based on a fourth parameter estimation model. The first controlling module 410 may input the image magnification and the one or more image quality parameters into the fourth parameter estimation model. The fourth parameter estimation model may estimate the location information based on the image magnification and the one or more image quality parameters. Exemplary fourth parameter estimation models may include convolutional neural networks (CNNs), artificial neural networks (ANNs), recurrent neural networks (RNNs), deep neural networks, or the like, or any combination thereof. For those skilled in the art, the process for training the model may be found in prior art, and not be described in detail. The fourth parameter estimation model may be stored in a storage medium (e.g., the storage device 150, and/or the storage 220) of the imaging system 100. The first controlling module 410 may obtain the fourth parameter estimation model from the storage medium.

In some embodiments, the first controlling module 410 may obtain, from a storage medium (e.g., the storage device 150, and/or the storage 220) of the imaging system 100, a fifth parameter table including a relationship among the location information, the image magnification, the one or more image quality parameters, the one or more first parameters of the detector 112, and the one or more second parameters of the X-ray generator 113. The first controlling module 410 may determine the one or more first parameters of the detector 112, the one or more second parameters of the X-ray generator 113, the image magnification, and the location information based on the one or more image quality parameters using the fifth parameter table.

In some embodiments, the first controlling module 410 may obtain, from a storage medium (e.g., the storage device 150, and/or the storage 220) of the imaging system 100, a fifth parameter estimation model. The first controlling module 410 may input the one or more image quality parameters into the fifth parameter estimation model. The fifth parameter estimation model may estimate the one or more first parameters of the detector 112, the one or more second parameters of the X-ray generator 113, the image magnification, and the location information based on the one or more image quality parameters. Exemplary fifth parameter estimation models may include convolutional neural networks (CNNs), artificial neural networks (ANNs), recurrent neural networks (RNNs), deep neural networks, or the like, or any combination thereof.

After adjusting the locations of the X-ray generator 113, the detector 112, or the ROI, the first controlling module 410 may direct the imaging device 110 to scan the ROI under the location information, the second configuration specified by the one or more first parameters, and the second configuration specified by the one or more second parameters to generate an image that satisfies the image magnification and the one or more image quality parameters.

It should be noted that the description of the process 800 is provided for the purposes of illustration, and not intended to limit the scope of the present disclosure. For persons having ordinary skills in the art, various variations and modifications may be conducted under the teaching of the present disclosure. However, those variations and modifications may not depart from the protecting of the present disclosure.

In some embodiments, different scan objects may have different X-ray attenuation. For example, bony tissue has relatively high X-ray attenuation, which needs a relatively high X-ray dose (e.g., obtained by adjusting exposure parameters such as a tube voltage and/or a tube current of the X-ray generator 113 in FIG. 1) to generate an image having target brightness. As another example, adipose tissue has relatively low X-ray attenuation, which needs a relatively low X-ray dose (e.g., obtained by adjusting exposure parameters such as a tube voltage and/or a tube current of the X-ray generator 113 in FIG. 1) to generate an image having the same target brightness. Therefore, the processing device 140 (e.g., the second controlling module 420) may perform process 900 and/or process 1000 to generate an image satisfying target brightness (e.g., the brightness of the generated image is equal to the target brightness, or the difference between the brightness of the generated image and the target brightness is less than a brightness threshold, such as 0.1) by quickly adjusting one or more exposure parameters of the imaging device 110 in FIG. 1. The process for quickly and automatically adjusting one or more exposure parameters of the imaging device 110 as disclosed herein (e.g., using a thickness model), compared to manual adjustment by, e.g., trial and error based on experience, may reduce the number (or count) of unsatisfactory imaging to provide unsatisfactory images, thereby reducing the X-ray dose that the scan object receives.

Figure 9:
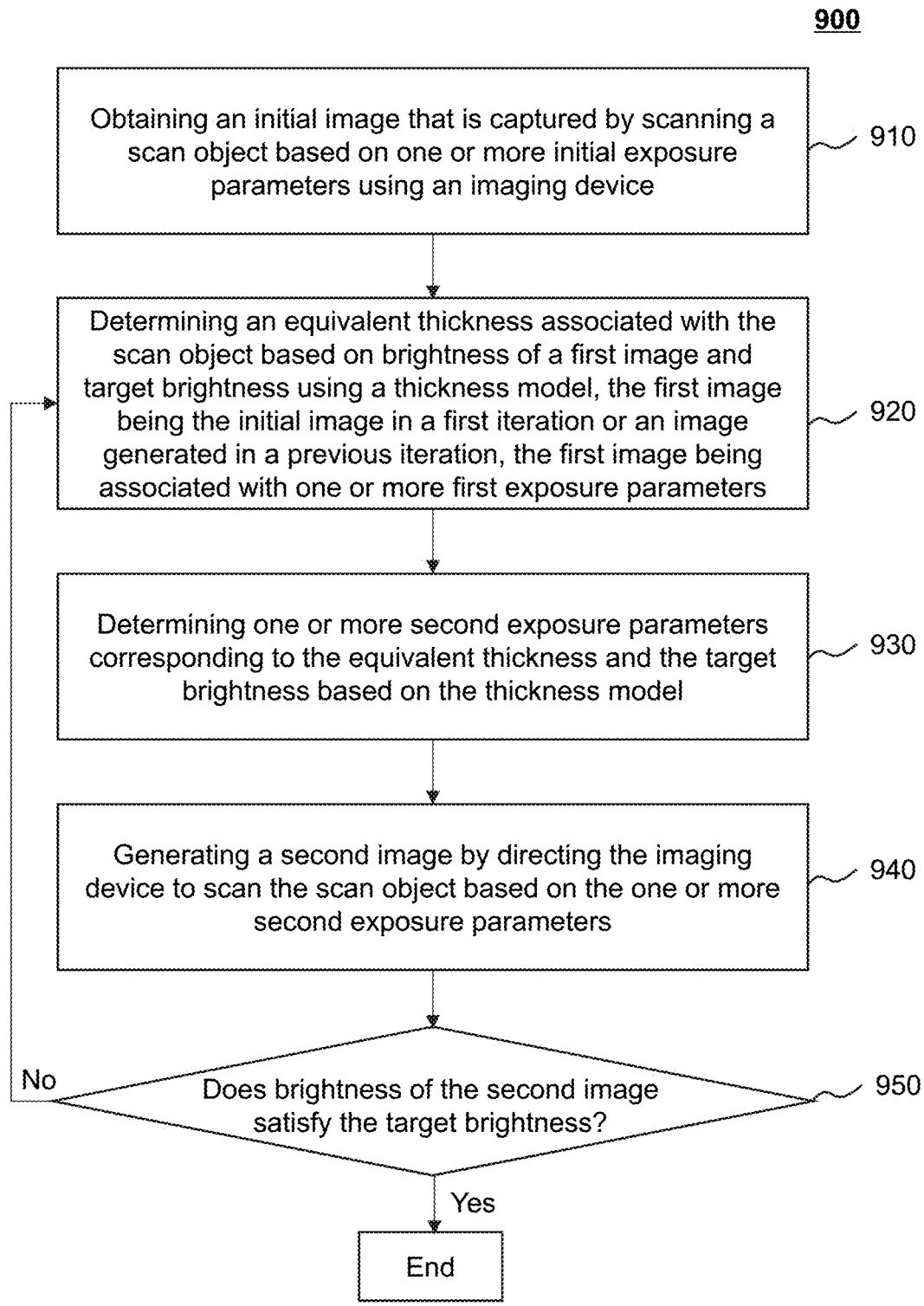
FIG. 9 is a flowchart illustrating an exemplary process for medical imaging according to some embodiments of the present disclosure.

FIG. 9 is a flowchart illustrating an exemplary process for medical imaging according to some embodiments of the present disclosure. In some embodiments, one or more operations of the process 900 illustrated in FIG. 9 for medical imaging may be implemented in the imaging system 100 illustrated in FIG. 1. For example, the process 900 illustrated in FIG. 9 may be stored in a storage medium (e.g., the storage device 150, and/or the storage 220) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules/units/blocks of the processing device 140 illustrated in FIGS. 4-6). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

In 910, the second controlling module 420 (e.g., the acquisition unit 422) may obtain an initial image that is captured by scanning a scan object (e.g., the ROI 1102 in FIG. 12) based on one or more initial exposure parameters using an imaging device (e.g., the imaging device 110 in FIG. 1).

In some embodiments, the second controlling module 420 may obtain the initial image from a storage medium (e.g., the storage device 150, and/or the storage 220) of the imaging system 100. In some embodiments, the second controlling module 420 may obtain the initial image in real time during a scan process. For example, a plurality of images have been generated during a scan process of scanning the scan object. The initial image may be any one of the plurality of images, such as the first image or the last image.

In some embodiments, the second controlling module 420 may determine the brightness of the initial image. As used herein, the brightness of an image may refer to an average value of gray values of pixels in at least a portion (e.g., a region of interest) of the image.

The exposure parameters of the imaging device 110 may include a tube voltage of the X-ray generator 113, a tube current of the X-ray generator 113, a filtration mode, a beam field size, a radiation time, a source image distance (SID), or the like, or any combination thereof. The tube voltage refers to a voltage between a cathode of the X-ray generator 113 and an anode of the X-ray generator 113 during the X-ray generator 113 is emitting X-ray beams. The tube current refers to a current between the cathode of the X-ray generator 113 and the anode of the X-ray generator 113 during the X-ray generator 113 is emitting X-ray beams. The filtration mode may include a filter material placed in front of the X-ray generator 113 in order to reduce the intensity of particular X-ray wavelengths from its spectrum and selectively alter the distribution of X-ray wavelengths within a given x-ray beam. Exemplary filter materials may include aluminum, copper, silver, iron, and so on. For filters of different filter materials, the thickness of the filters may be different, which causes different doses of the X-rays transmitted through the filters. The beam field size may be a variable parameter. If the beam field size is relatively large, the generated image may have a relatively large FOV and relatively poor image details, and the scan object may receive a relatively large X-ray dose. If the beam field size is relatively small, the generated image may have a relatively small FOV and relatively rich image details, and the scan object may receive a relatively small X-ray dose.

In some embodiments, the imaging device 110 may scan the scan object under the one or more initial exposure parameters to generate the initial image. For example, if the initial image is the first image during a scan process, the one or more initial exposure parameters may be assigned default values of the imaging system 100 or be preset by a user (e.g., an operator, a doctor, or an imaging technician) of the imaging system 100 through, for example, the I/O 230 and/or the I/O 350.

In some embodiments, if the brightness of the initial image does not satisfy target brightness, the second controlling module 420 may perform an iteration process including one or more iterations until an image of which brightness satisfies the target brightness is generated. For example, each iteration may include operations 920-950.

In 920, the second controlling module 420 (e.g., the equivalent thickness determination unit 424) may determine an equivalent thickness associated with the scan object based on brightness of a first image and the target brightness using a thickness model. The first image may be the initial image in a first iteration of the one or more iterations or an image acquired in a previous iteration. The first image may be generated by scanning the scan object based on one or more first exposure parameters using the imaging device 110. For example, if the first image is the initial image in the first iteration of the one or more iterations of the iteration process, the one or more first exposure parameters may be the one or more initial exposure parameters.

In some embodiments, the thickness model may indicate a relationship among a thickness of a sample (e.g., a water phantom, a polymethyl methacrylate (PMMA) phantom) having X-ray attenuation similar to a human body, the one or more exposure parameters, and brightness of an image generated by scanning the sample corresponding to the thickness under the one or more exposure parameters using the imaging device 110. The thickness model may be take the form of a table, an equation, a machine learning model, or the like, or any combination thereof.

In some embodiments, the thickness model may be generated online or offline. In some embodiments, the thickness model may be generated by the processing device 140 (e.g., the second controlling module 420) or a third-party device communicating with the imaging system 100. In some embodiments, the processing device 140 or a third-party device may generate the thickness model in advance and store the thickness model in a storage medium (e.g., the storage device 150, and/or the storage 220 of the processing device 140) of the imaging system 100 or from the third-party device or a storage device communicating with the third-party device where the thickness model is saved. When determining the equivalent thickness, the processing device 140 may obtain the thickness model from the storage medium of the imaging system 100. In some embodiments, when determining an equivalent thickness, the processing device 140 may generate the thickness model online. In some embodiments, when the processing device 140 determines the equivalent thickness, the third-party device may generate the thickness model online and transmit the thickness model to the processing device 140.

In some embodiments, the imaging device 110 may scan a plurality of samples having different thicknesses under different sample exposure parameters to generate a plurality of sample images having different brightness. During the scan process, and the process for generating the plurality of sample images, the different thicknesses, the different sample exposure parameters, and the different brightness may be recorded, and a plurality of parameter groups may be obtained. Each of the plurality of parameter groups may include a thickness of a sample, one or more sample exposure parameters, and the brightness of a sample image generated by scanning the sample of the thickness under the one or more sample exposure parameters using the imaging device 110. In some embodiments, if there are two or more parameter groups including different exposure parameters but the same thickness and the same brightness, one of the two or more parameter groups related to which the radiation power is minimum and/or the imaging quality is highest may be kept, and the remaining of the two or more parameter groups may be removed.

In some embodiments, the thickness module may be determined by curve fitting of the plurality of parameter groups, constructing a table using the plurality of parameter groups, or training the plurality of parameter groups using a machine learning technique.

In some embodiments, the second controlling module 420 may determine a ratio of the brightness of the first image to target brightness. For example, if the brightness of the first image is 50 and the target brightness is 100, the ratio is 0.5 (i.e., 50/100). Alternatively, the second controlling module 420 may determine a ratio of the target brightness to the brightness of the first image. For example, if the brightness of the first image is 50 and the target brightness is 100, the ratio is 2 (i.e., 100/50). The second controlling module 420 may determine an equivalent thickness based on the ratio and a reference thickness corresponding to the target brightness and the one or more first exposure parameters using the thickness model. For example, if the second controlling module 420 determines a ratio of the brightness of the first image to the target brightness, the second controlling module 420 may determine the equivalent thickness by dividing the reference thickness by the ratio. As another example, if the second controlling module 420 determines a ratio of the target brightness to the brightness of the first image, the second controlling module 420 may determine the equivalent thickness by multiplying the reference thickness by the ratio.

Alternatively or additionally, the second controlling module 420 may determine the equivalent thickness based on the brightness of the first image and the one or more first exposure parameters. For example, if the thickness model is a table, the second controlling module 420 may determine a thickness corresponding to the brightness of the first image and the one or more first exposure parameters as the equivalent thickness by searching the table. As another example, if the thickness model is a machine learning model, the second controlling module 420 may input the brightness of the first image and the one or more first exposure parameters to the machine learning model. The machine learning model may output the equivalent thickness based on the brightness of the first image and the one or more first exposure parameters.

In 930, the second controlling module 420 (e.g., exposure parameter determination unit 426) may determine one or more second exposure parameters corresponding to the equivalent thickness and the target brightness based on the thickness model.

Merely by way of example, Table. 1 illustrates an exemplary thickness model corresponding to the target brightness that is 20, and Table. 2 illustrates an exemplary thickness model corresponding to the target brightness that is 15. As shown in Table 1 and Table 2, the exemplary exposure parameters include the tube voltage and the tube current.

TABLE 1

Exemplary thickness model corresponding to the target brightness that is 20

| | Tube Voltage/kV | | | | |
|---|---|---|---|---|---|
| | 40 | 45 | 50 | 60 | 80 |
| Tube Current/mA | 10 | 11 | 12 | 15 | 20 |
| Thickness/mm | 5 | 10 | 13.3 | 14.76 | 15 |

TABLE 2

Exemplary thickness model corresponding to the target brightness that is 15

| | Tube Voltage/kV | | | | |
|---|---|---|---|---|---|
| | 40 | 45 | 50 | 60 | 80 |
| Tube Current/mA | 10 | 11 | 12 | 15 | 20 |
| Thickness/mm | 7.5 | 13.3 | 15 | 16.5 | 18 |

As illustrated in Table. 1 and Table 2, the thickness model indicates a relationship between the thicknesses and the exposure parameters (e.g., the tube voltage and the tube current). For example, as shown in Table 1, when the thickness of the sample is 5 mm, the tube voltage is 40 kV and the tube current is 10 mA in order to generate an image of the sample having the brightness of 20. As another example, when the thickness of the sample is 14.76 mm, the tube voltage is 60 kV and the tube current is 15 mA in order to generate an image of the sample having the brightness of 20.

It should be noted that the exposure parameters and the values in Table 1 and Table 2 may be just for illustration purposes, and not intended to limit the scope of the present disclosure. Besides the tube voltage and the tube current, the exposure parameters may also include the SID, the radiation time, the field beam size, and so on. In some embodiments, the more parameters the exposure parameters include, the lower the iteration count of the iteration process may be, and the lower X-ray dose the scan object may receive.

Merely by way of example, the first image may be generated by the imaging system 100 under the tube voltage of 45 kV and the tube current of 11 mA. The target brightness is 20. The second controlling module 420 may determine that the brightness of the first image is 15. The second controlling module 420 may determine the ratio of the target brightness to the brightness of the first image is 1.33 (i.e., 20/15). The second controlling module 420 may determine the reference thickness as 10 mm based on the thickness module illustrated in Table 1. The second controlling module 420 may designate the product of the ratio and the reference thickness as the equivalent thickness. The equivalent thickness is 13.3 mm (i.e., 1.33×10 mm). The second controlling module 420 may determine the one or more second exposure parameters as (50, 12), i.e., the tube voltage is 50 kV and the tube current is 12 mA, based on the equivalent thickness of 13.3 mm and the target brightness of 20 using the thickness model illustrated in Table. 1.

Merely by way of example, the first image may be generated by the imaging system 100 under the tube voltage of 45 kV and the tube current of 11 mA. The target brightness is 20. The second controlling module 420 may determine that the brightness of the first image is 15. The second controlling module 420 may determine that the equivalent thickness is 13.3 mm based on the brightness of the first image of 15, the tube voltage of 45 kV, and the tube current of 11 mA using Table 2. The second controlling module 420 may determine the one or more second exposure parameters as (50, 12), i.e., the tube voltage is 50 kV and the tube current is 12 mA, based on the equivalent thickness of 13.3 mm and the target brightness of 20 using the thickness model illustrated in Table. 1.

In some embodiments, during the process for determining the equivalent thickness using Table 2, if the one or more first exposure parameters of the first image are not included in Table 2, the second controlling module 420 may determine the equivalent thickness based on, for example, an interpolation algorithm. Exemplary interpolation algorithms may include Lagrange interpolation, Newton interpolation, Hermite interpolation, piecewise interpolation, spline interpolation, linear interpolation, or the like, or a combination thereof. For example, if the one or more first exposure parameters are (55, 13) (i.e., the tube voltage is 55 kV and the tube current is 13 mA) that is not included in Table 2, the second controlling module 420 may determine the equivalent thickness based on the exposure parameters of (60, 15) and (50, 12) using the linear interpolation.

In some embodiments, if the second controlling module 420 determines an equivalent thickness that is not included in Table 1, the second controlling module 420 may determine the one or more second exposure parameters based on, for example, an interpolation algorithm. For example, if the second controlling module 420 determines an equivalent thickness of 12 mm that is not included in Table 1, the second controlling module 420 may determine the one or more second exposure parameters based on the exposure parameters of (45, 11) and (50, 12) using the linear interpolation.

In 940, the second controlling module 420 (e.g., the scanning unit 428) may generate a second image by directing the imaging device 110 to scan the scan object based on the one or more second exposure parameters.

In 950, the second controlling module 420 (e.g., the scanning unit 428) may determine whether the brightness of the second image satisfies the target brightness. In response to a determination that the brightness of the second image satisfies (e.g., the brightness of the second image is equal to the target brightness, or the difference between the brightness of the second image and the target brightness is less than a brightness threshold, such as 0.1) the target brightness, the second controlling module 420 may terminate the iteration process. In response to a determination that the brightness of the second image does not satisfy the target brightness, the second controlling module 420 may initiate a new iteration by repeating operations 920-950. In some embodiments, an iteration count of the iteration process may be lower than or equal to 5.

Merely by way of example, if the brightness of the second image in a first iteration is 18, which is less than the target brightness of 20, the second controlling module 420 may initiate a second iteration by repeating operations 920-950. In the second iteration, the second controlling module 420 may determine the ratio of the target brightness of 20 to the brightness of 18 as 1.11 (i.e., 20/18=1.11), and determine the reference thickness as 13.3 mm based on the target brightness of 20 and the exposure parameters of (50, 12) (i.e., the tube voltage is 50 kV and the tube current is 12 mA) using the thickness model in Table 1. The second controlling module 420 may determine the equivalent thickness as 14.76 mm (i.e., 1.11×13.3=14.76) based on the ratio of 1.11 and the reference thickness of 13.3 mm. The second controlling module 420 may determine one or more corresponding exposure parameters of the equivalent thickness of 14.76 mm as (60, 15) (i.e., the tube voltage is 60 kV and the tube current is 15 mA) using the thickness model in Table 1. The second controlling module 420 may direct the imaging device 110 to scan the scan object under the tube voltage of 60 kV and the tube current of 15 mA to generate an image. If the brightness of the current image satisfies the target brightness of 20, the second controlling module 420 may terminate the process 900 and output the current image as a target image. If the brightness of the current image does not satisfy the target brightness of 20, the second controlling module 420 may initiate a third iteration by repeating operations 920-950.

For example, for a C-arm X-ray device, when the user of the imaging system 100 presses a button to start emitting X-rays, the processing device 140 may perform the process 900 automatically until an image satisfying the target brightness is generated. During the scan process, 3-4 images may be generated, which reduces 85% X-ray dose that the scan object receives compared to the process for manually controlling the imaging device 110 to generate an image satisfying the target brightness.

In some embodiments, the initial image may be obtained by performing the process 700 and/or the process 800. For example, the first controlling module 410 may determine the one or more first parameters of the detector 112, the one or more second parameter of the X-ray generator 113, and the location information associated with the detector 112, the X-ray generator 113, and the ROI of the scan object based on the one or more image quality parameters (e.g., the target brightness) by performing the process 700 and/or the process 800, and generate an image by directing the imaging device 110 to scan the ROI based on the one or more first parameters of the detector 112, the one or more second parameter of the X-ray generator 113, and the location information. The second controlling module 420 may determine the generated image as the initial image and perform the process 900 based on the initial image.

Merely by way of example, the first controlling module 410 may determine the image magnification based on the location information. The first controlling module 410 may determine the pixel size of the detector 112 and the focal size of the X-ray generator 113 based on the one or more quality image parameters and the image magnification, and determine the X-ray dose on the detector 112 based on the pixel size of the detector 112 and the focal size of the X-ray generator 113. The first controlling module 410 may generate an image by directing the imaging device 110 to scan the scan object based on the pixel size of the detector 112, the focal size of the X-ray generator 113, the X-ray dose on the detector 112, and the location information. The second controlling module 420 may determine the generated image as the initial image and perform the process 900 based on the initial image to generate an image satisfying the target brightness. Compared to the process 900, the count of the iterations for generating an image satisfying the target brightness in the process that combines the process 700

(and/or the process 800) and the process 900 may be fewer, which further reduces the X-ray dose that the scan object receives.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 10:
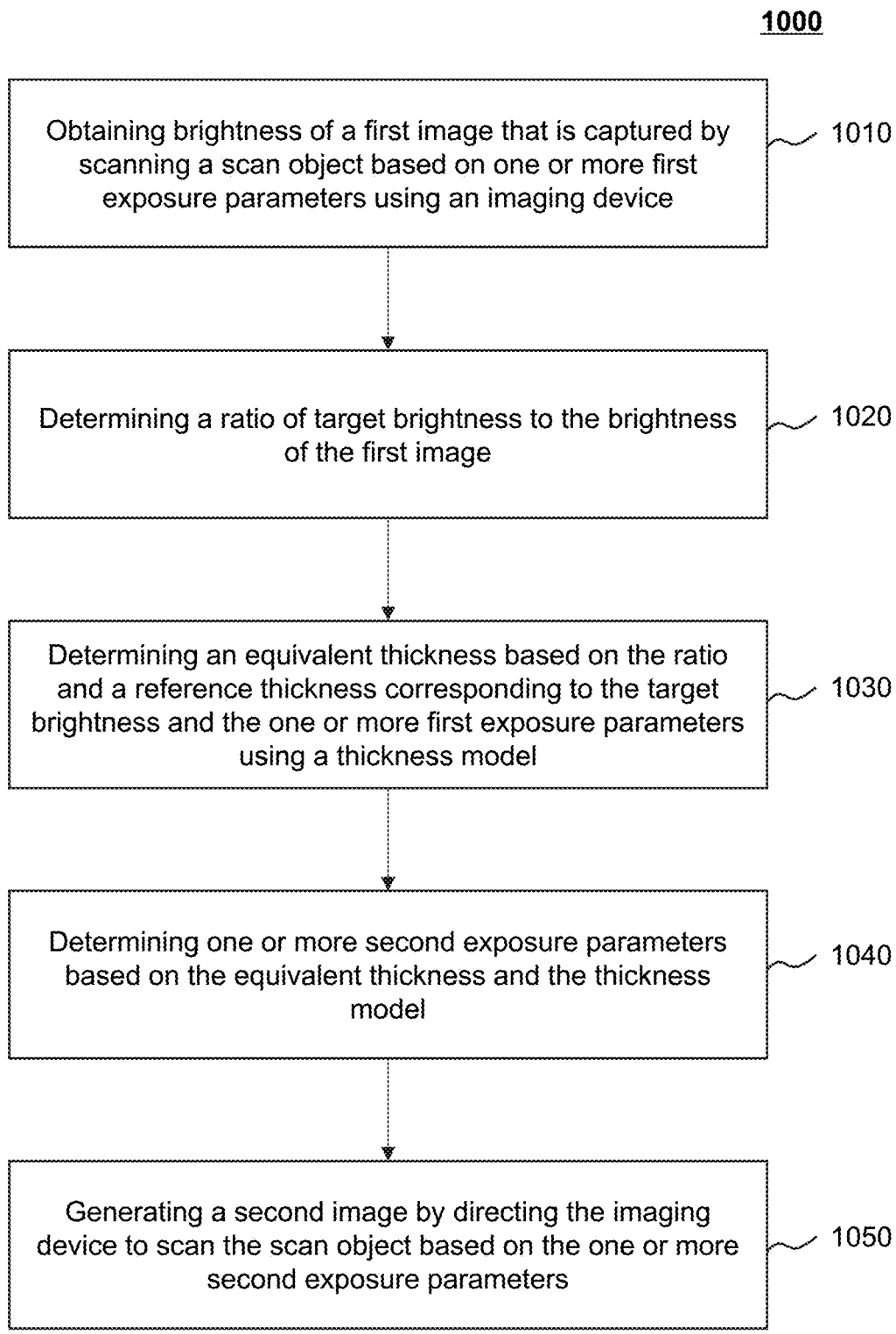
FIG. 10 is a flowchart illustrating an exemplary process for medical imaging according to some embodiments of the present disclosure.

FIG. 10 is a flowchart illustrating an exemplary process for medical imaging in one iteration according to some embodiments of the present disclosure. In some embodiments, one or more operations of the process 1000 illustrated in FIG. 10 for medical imaging may be implemented in the imaging system 100 illustrated in FIG. 1. For example, the process 1000 illustrated in FIG. 10 may be stored in a storage medium (e.g., the storage device 150, and/or the storage 220) of the imaging system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules/units/blocks of the processing device 140 illustrated in FIGS. 4-6). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting. In some embodiments, operations 920-940 of the process 900 in FIG. 9 may be performed based on the process 1000.

In 1010, the second controlling module 420 (e.g., the acquisition unit 422) may obtain a brightness of a first image that is captured by scanning a scan object based on one or more first exposure parameters using an imaging device (e.g., the imaging device 110 in FIG. 1). The brightness of the first image refers to an average value of gray values of pixels in at least a portion (e.g., a region of interest) of the first image.

In 1020, the second controlling module 420 (e.g., the equivalent thickness determination unit 424) may determine a ratio of the brightness of the first image to target brightness. For example, if the brightness of the first image is 50 and the target brightness is 100, the ratio is 0.5 (i.e., 50/100). Alternatively, the second controlling module 420 may determine a ratio of the target brightness to the brightness of the first image. For example, if the brightness of the first image is 50 and the target brightness is 100, the ratio is 2 (i.e., 100/50).

In 1030, the second controlling module 420 (e.g., the equivalent thickness determination unit 424) may determine an equivalent thickness based on the ratio and a reference thickness corresponding to the target brightness and the one or more first exposure parameters using a thickness model. For example, if the second controlling module 420 determines a ratio of the brightness of the first image to the target brightness, the second controlling module 420 may determine the equivalent thickness by dividing the reference thickness by the ratio. As another example, if the second controlling module 420 determines a ratio of the target brightness to the brightness of the first image, the second controlling module 420 may determine the equivalent thickness by multiplying the reference thickness by the ratio.

The thickness model may indicate a relationship among a thickness of a sample (e.g., a water phantom, a polymethyl methacrylate (PMMA) phantom) having X-ray attenuation similar to a human body, the one or more exposure parameters, and brightness of an image generated by scanning the sample corresponding to the thickness under the one or more exposure parameters using the imaging device 110. The thickness model may include a table, an equation, a machine learning model, or the like, or any combination thereof.

In 1040, the second controlling module 420 (e.g., the exposure parameter determination unit 426) may determine one or more second exposure parameters corresponding to the equivalent thickness and the target brightness based on the thickness model.

Merely by way of example, the first image may be generated by the imaging system 100 under the tube voltage of 45 kV and the tube current of 11 mA. The target brightness is 20. The second controlling module 420 may determine that the brightness of the first image is 15. The second controlling module 420 may determine the ratio of the target brightness to the brightness of the first image is 1.33 (i.e., 20/15). The second controlling module 420 may determine the reference thickness as 10 mm based on the thickness module illustrated in Table 1. The second controlling module 420 may designate the product of the ratio and the reference thickness as the equivalent thickness. The equivalent thickness is 13.3 mm (i.e., 1.33×10 mm). The second controlling module 420 may determine the one or more second exposure parameters as (50, 12), i.e., the tube voltage is 50 kV and the tube current is 12 mA, based on the equivalent thickness of 13.3 mm and the target brightness of 20 using the thickness model illustrated in Table. 1.

In 1050, the second controlling module 420 (e.g., the scanning unit 428) may generate a second image by directing the imaging device 110 to scan the scan object based on the one or more second exposure parameters.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 11 is a schematic diagram illustrating an exemplary imaging device according to some embodiments of the present disclosure. As illustrated in FIG. 11, the imaging device 1100 may include a gantry 1111, a detector 1112, an X-ray generator 1113, and a motion controller 1106.

As shown in FIG. 11, the detector 112 and the X-ray generator 1113 may be oppositely mounted on the gantry 1111. The gantry 1111 may support the detector 1112 and the X-ray generator 1113. There may be a space between the detector 1112 and the X-ray generator 1113. The space may be configured to hold an ROI (e.g., an ROI 1102) of a scan object. The ROI 1102 may be placed on a scan table (e.g., the scanning table 114 in FIG. 1) and moved into a detection tunnel (e.g., the space) of the imaging device 1100. In some embodiments, the central controller 1104 may be configured to control motions of the detector 112, the X-ray generator 1113, and the ROI 1102 (e.g., the scan table).

The SID refers to a distance between the focal spot of the X-ray generator 1113 and the detector 1112 (e.g., an imaging region of the detector 1112). The SOD) refers to a distance between the focal spot of the X-ray generator 1113 and the ROI 1102. The IOD refers to a distance between the ROI 1102 and the detector 1112 (e.g., an imaging region of the detector 1112). In some embodiments, the SID may be equal to a sum of the SOD and IOD, and the focal spot of the X-ray generator 1113, the center of the imaging region of the detector 1112, and the center of the ROI of the scan object may be in a straight line. In some embodiments, the image magnification may be determined by dividing the SID by the SOD (e.g., SID/SOD).

In some embodiments, the imaging device 1100 may be communicated with a central controller 1104, an image processor 1108, and a display 1110. In some embodiments, the central controller 1104, the image processor 1108, and the display 1110 may be part of the processing device 140 in FIG. 1. In some embodiments, the first controlling module 410 and/or the second controlling module 420 may be implemented on the central controller 1104, the image processor 1108, or the display 1110.

For example, the central controller 1104 may determine the location information associated with the detector 1112, the X-ray generator 1113, and the ROI 1102 by performing the process 800 in FIG. 8 and transmit the location information to the motion controller 1106. The motion controller 1106 may drive the X-ray generator 1113, the detector 1112, or the ROI 1102 (e.g., the scan table) to corresponding locations based on the location information.

As another example, the central controller 1104 may determine one or more first parameters of the detector 1112 and one or more second parameters of the X-ray generator 1113 by performing the process 700 in FIG. 7 or operation 810 of the process 800 in FIG. 8. The central controller 1104 may adjust the parameters of the detector 1112 based on the one or more first parameters and adjust the parameters of the X-ray generator 1113 based on the one or more second parameters.

As still another example, the central controller 1104 may determine one or more exposure parameters of the imaging device 1100 by performing the process 900 in FIG. 9 and/or the process 1000 in FIG. 10. The central controller 1104 may adjust the parameters of the detector 1112 and/or the X-ray generator 1113 based on the one or more exposure parameters.

In some embodiments, the central controller 1104 may direct the imaging device 1100 to scan the ROI 1102 under the location information, the one or more first parameters of the detector 1112, the one or more second parameters of the X-ray generator 1113, or the one or more exposure parameters of the imaging device 1100. During the scan process, the X-ray generator 1113 may emit X-rays. The X-rays may pass through the ROI 1102 and be received by the detector 1112. The detector 1112 may transform light signals of the X-rays into electronic signals. The electronic signals may be transformed into digital signals by an analog-digital converter (ADC). The imaging device 1100 may transmit the digital signals to the image processor 1108. The image processor 1108 may process the digital signals to generate an image. The image may be displayed in the display 1110. In some embodiments, the display 1110 may also display the location information associated with the detector 1112, the X-ray generator 1113, and the ROI 1102. In some embodiments, the user of the imaging system 100 may input the predetermined location information, the one or more first preset parameters of the detector 1112, the one or more second preset parameters of the X-ray generator 1113, or the one or more image quality parameters (e.g., the image contrast, the image resolution, or the target brightness) through the display 1110.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for medical imaging, comprising:
   an imaging device including an X-ray generator and a detector;
   at least one storage device including a set of instructions; and
   at least one processor in communication with the at least one storage device, wherein when executing the set of instructions, the at least one processor is directed to cause the system to:
   obtain location information associated with the X-ray generator of the imaging device, the detector of the imaging device, and a region of interest (ROI) of a scan object;
   determine image magnification based on the location information;
   according to image quality conditions, determine one or more first parameters of the detector and one or more second parameters of the X-ray generator based on the image magnification, the one or more first parameters of the detector being different from one or more first preset parameters of the detector, the one or more second parameters of the X-ray generator being different from one or more second preset parameters of the X-ray generator; and
   generate an image of the image magnification by directing the imaging device to scan the ROI based on the one or more first parameters of the detector and the one or more second parameters of the X-ray generator.

2. The system of claim 1, wherein the location information associated with the X-ray generator, the detector, and the ROI includes at least one of a source image distance (SID), a source object distance (SOD), or an image object distance (IOD).

3. The system of claim 1, wherein the one or more first parameters of the detector include at least one of a pixel size, an image readout mode, an integration time, a frame rate, or X-ray dose on the detector; and
   the one or more second parameters of the X-ray generator include at least one of a focal spot size, a pulse frequency, a pulse width, or a radiation power.

4. The system of claim 3, wherein according to the image quality conditions, to determine the one or more first parameters of the detector of the imaging device and the one or more second parameters of the x-ray generator of the imaging device based on the image magnification, the at least one processor is directed to cause the system to:

determine the pixel size and the focal spot size based on the image magnification and one or more image quality parameters; and determine the X-ray dose on the detector based on the pixel size and the focal spot size.

5. The system of claim 4, wherein the one or more image quality parameters include at least one of an image contrast or an image resolution.

6. The system of claim 4, wherein according to the image quality conditions, to determine the one or more first parameters of the detector of the imaging device and the one or more second parameters of the X-ray generator of the imaging device based on the image magnification, the at least one processor is further directed to cause the system to:

obtain information associated with a target in the ROI; and determine the one or more first parameters of the detector and the one or more second parameters of the X-ray generator based on the image magnification and the information associated with the target in the ROI.

7. The system of claim 6, wherein the information associated with the target in the ROI includes at least one of a composition of the target or X-ray attenuation through the target.

8. A system for medical imaging, comprising:
an imaging device including an X-ray generator and a detector;
at least one storage device including a set of instructions; and
at least one processor in communication with the at least one storage device, wherein when executing the set of instructions, the at least one processor is directed to cause the system to:
obtain one or more image quality parameters;
determine one or more first parameters of the detector of the imaging device and one or more second parameters of the X-ray generator of the imaging device based on the one or more image quality parameters, the one or more first parameters of the detector being different from one or more first preset parameters of the detector, the one or more second parameters of the X-ray generator being different from one or more second preset parameters of the X-ray generator;
determine image magnification based on the one or more first parameters of the detector and the one or more second parameters of the X-ray generator;
determine location information associated with the X-ray generator, the detector, and a region of interest (ROI) of a scan object; and
adjust, based on the location information, at least one of the X-ray generator, the detector, or the ROI.

9. The system of claim 8, wherein the location information associated with the X-ray generator, the detector, and the ROI includes at least one of a source image distance (SID), a source object distance (SOD), or an image object distance (IOD).

10. The system of claim 8, wherein the one or more first parameters of the detector include at least one of a pixel size, an image readout mode, an integration time, a frame rate, or X-ray dose on the detector;
the one or more second parameters of the x-ray generator include at least one of a focal spot size, a pulse frequency, a pulse width, or a radiation power; and
the one or more image quality parameters include at least one of an image contrast or an image resolution.

11. The system of claim 10, wherein to determine the one or more first parameters of the detector of the imaging device and the one or more second parameters of the x-ray generator of the imaging device based on the one or more image quality parameters, the at least one processor is directed to cause the system to:
determine the pixel size, the focal spot size, and the X-ray dose on the detector based on the image resolution and the image contrast.

12. The system of claim 8, wherein when executing the set of instructions, the at least one processor is further directed to cause the system to:
generate an image of the image magnification by directing the imaging device to scan the ROI based on the one or more first parameters of the detector, the one or more second parameters of the X-ray generator, and the location information.

13. A system for medical imaging, comprising:
an imaging device including an X-ray generator and a detector;
at least one storage device including a set of instructions; and
at least one processor in communication with the at least one storage device, wherein when executing the set of instructions, the at least one processor is directed to cause the system to:
obtain an initial image that is captured by scanning a scan object based on one or more initial exposure parameters using the imaging device; and
perform an iteration process including one or more iterations until an image whose brightness satisfies a target brightness is generated, each of the one or more iterations including:
determining, according to a thickness model, an equivalent thickness associated with the scan object based on a brightness of a first image and the target brightness, the first image being the initial image in a first iteration of the one or more iterations or an image generated in a previous iteration, the first image being associated with one or more first exposure parameters;
determining one or more second exposure parameters corresponding to the equivalent thickness and the target brightness based on the thickness model; and
generating a second image by directing the imaging device to scan the scan object based on the one or more second exposure parameters using the imaging device.

14. The system of claim 13, wherein each of the one or more iterations further includes:
determining that a brightness of the second image satisfies the target brightness; and
terminating the iteration process in response to a determination that the brightness of the second image satisfies the target brightness.

15. The system of claim 13, wherein each of the one or more iterations further includes:
determining that a brightness of the second image is lower than the target brightness; and
initiating a next iteration of the iteration process in response to a determination that the brightness of the second image is lower than the target brightness.

16. The system of claim 13, wherein an iteration count of the iteration process is lower than or equal to 5.

17. The system of claim 13, wherein the determining of the equivalent thickness associated with the scan object based on the brightness of the first image and the target brightness according to the thickness model includes:
- determining a ratio of the target brightness to the brightness of the first image;
- determining a reference thickness corresponding to the target brightness and the one or more first exposure parameters associated with the first image based on the thickness model; and
- determining the equivalent thickness based on the ratio and the reference thickness corresponding to the target brightness and the one or more first exposure parameters associated with the first image.

18. The system of claim 13, wherein the one or more first exposure parameters or the one or more second exposure parameters include at least one of a tube voltage associated with the X-ray generator, a tube current associated with the X-ray generator, a filtration mode, a beam field size, a radiation time, or a source image distance (SID).

19. The system of claim 13, wherein to obtain the initial image that is captured by scanning the scan object based on the one or more initial exposure parameters using the imaging device, the at least one processor is directed to cause the system to:
- obtain location information associated with the X-ray generator of the imaging device, the detector of the imaging device, and a region of interest (ROI) of the scan object;
- determine image magnification based on the location information;
- determine one or more first parameters of the detector and one or more second parameters of the X-ray generator based on the image magnification and the target brightness; and
- generate the initial image of the image magnification by directing the imaging device to scan the ROI based on the one or more first parameters of the detector and the one or more second parameters of the X-ray generator.

20. The system of claim 13, wherein to obtain the initial image that is captured by scanning the scan object based on the one or more initial exposure parameters using the imaging device, the at least one processor is directed to cause the system to:
- determine one or more first parameters of the detector of the imaging device and one or more second parameters of the X-ray generator of the imaging device based on the target brightness;
- determine image magnification based on the one or more first parameters of the detector and the one or more second parameters of the X-ray generator;
- determine location information associated with the X-ray generator, the detector, and an ROI of the scan object;
- adjust the X-ray generator, the detector, or the ROI based on the location information; and
- generate the initial image of the image magnification by directing the imaging device to scan the ROI based on the one or more first parameters of the detector and the one or more second parameters of the X-ray generator.

* * * * *